(12) United States Patent
Dixon et al.

(10) Patent No.: US 11,674,133 B2
(45) Date of Patent: Jun. 13, 2023

(54) METHODS AND COMPOSITIONS FOR EXTRACTING NUCLEIC ACIDS USING FERRIC OXIDE PARTICLES

(71) Applicant: Becton, Dickinson and Company, Franklin Lakes, NJ (US)

(72) Inventors: Eric P. Dixon, Cary, NC (US); John Joseph Harrington, Clayton, NC (US); Yutao Chen, Durham, NC (US); Nikhil Rao, San Francisco, CA (US); Ling Wang, Cary, NC (US)

(73) Assignee: BECTON, DICKINSON AND COMPANY, Franklin Lakes, NJ (US)

( * ) Notice: Subject to any disclaimer, the term of this patent is extended or adjusted under 35 U.S.C. 154(b) by 154 days.

(21) Appl. No.: 16/644,744

(22) PCT Filed: Sep. 10, 2018

(86) PCT No.: PCT/US2018/050157
§ 371 (c)(1),
(2) Date: Mar. 5, 2020

(87) PCT Pub. No.: WO2019/055331
PCT Pub. Date: Mar. 21, 2019

(65) Prior Publication Data
US 2020/0216830 A1  Jul. 9, 2020

Related U.S. Application Data

(60) Provisional application No. 62/558,074, filed on Sep. 13, 2017.

(51) Int. Cl.
*C12N 15/10* (2006.01)
*C12Q 1/6876* (2018.01)

(52) U.S. Cl.
CPC ....... *C12N 15/1013* (2013.01); *C12Q 1/6876* (2013.01); *C12Q 2521/537* (2013.01); *C12Q 2600/178* (2013.01)

(58) Field of Classification Search
CPC ............ C12N 15/1013; C12N 15/1006; C12Q 1/6876; C07H 1/08; C07H 21/00
See application file for complete search history.

(56) References Cited

U.S. PATENT DOCUMENTS

| 8,574,838 | B2 | 11/2013 | Zhang et al. |
| 8,980,552 | B2 | 3/2015 | Horlitz et al. |
| 9,499,869 | B2 | 11/2016 | Cohn et al. |
| 2004/0157223 | A1* | 8/2004 | Lou ........ C07H 21/04 536/25.4 |
| 2005/0287680 | A1 | 12/2005 | Venkatasubbarao et al. |
| 2005/0287682 | A1* | 12/2005 | Lizzi ........ B01L 3/5082 436/526 |
| 2009/0061497 | A1 | 3/2009 | Collis et al. |
| 2011/0275090 | A1* | 11/2011 | Hilligoss ........ C12N 15/1006 435/6.15 |
| 2012/0208189 | A1* | 8/2012 | Xu ........ C12Q 1/6876 536/25.4 |
| 2013/0287772 | A1* | 10/2013 | Halbert ........ A61P 17/00 435/6.12 |
| 2014/0341841 | A1 | 11/2014 | Jacob et al. |
| 2015/0184223 | A1* | 7/2015 | Keller ........ C12Q 1/6806 435/6.12 |
| 2015/0218620 | A1* | 8/2015 | Behlke ........ C12Q 1/6874 506/30 |
| 2015/0361483 | A1 | 12/2015 | Lo et al. |
| 2016/0097049 | A1* | 4/2016 | Qian ........ C12Q 1/6806 422/534 |
| 2018/0073066 | A1* | 3/2018 | Myers ........ C12N 15/11 |

FOREIGN PATENT DOCUMENTS

| CN | 102203251 A | 9/2011 |
| CN | 102834518 A | 12/2012 |
| CN | 103834637 A | 6/2014 |
| WO | WO201115975 A2 | 9/2011 |
| WO | WO2015094609 A1 | 6/2015 |

* cited by examiner

*Primary Examiner* — Narayan K Bhat
(74) *Attorney, Agent, or Firm* — Bret E. Field; Bozicevic, Field & Francis LLP

(57) ABSTRACT

Methods and compositions for extracting nucleic acids such as microRNAs (miRNAs) from biological samples are provided. Aspects of the methods include contacting a biological sample with proteinase K followed by contact with ferric oxide particles under acidic conditions to induce binding between the ferric oxide particles and nucleic acids (e.g., miRNAs) of the sample. In some cases, the ferric oxide particles are provided as part of a dissolvable film, which releases the ferric oxide particles upon solvation. In some embodiments, after nucleic acids bind to the ferric oxide particles, the particles are magnetically separated from the sample and are contacted with an alkaline elution buffer to release the nucleic acids.

10 Claims, 28 Drawing Sheets

Figure 3 (Cont. 1)
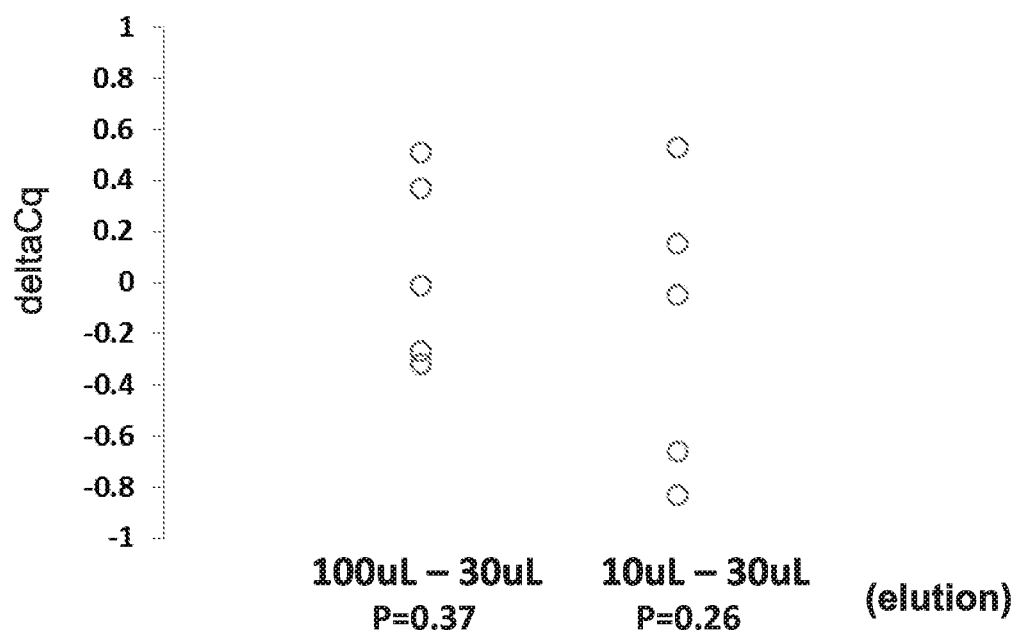
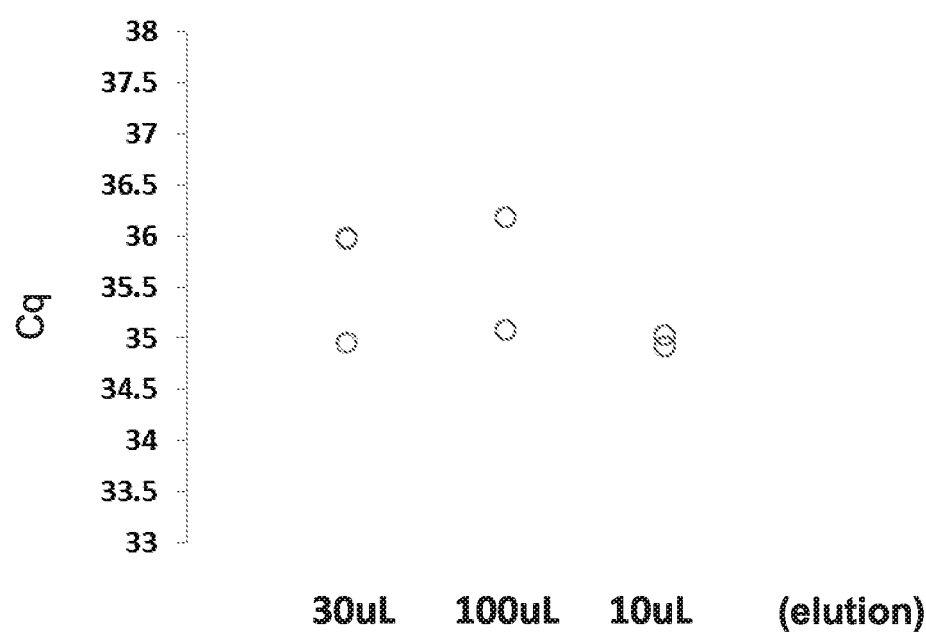

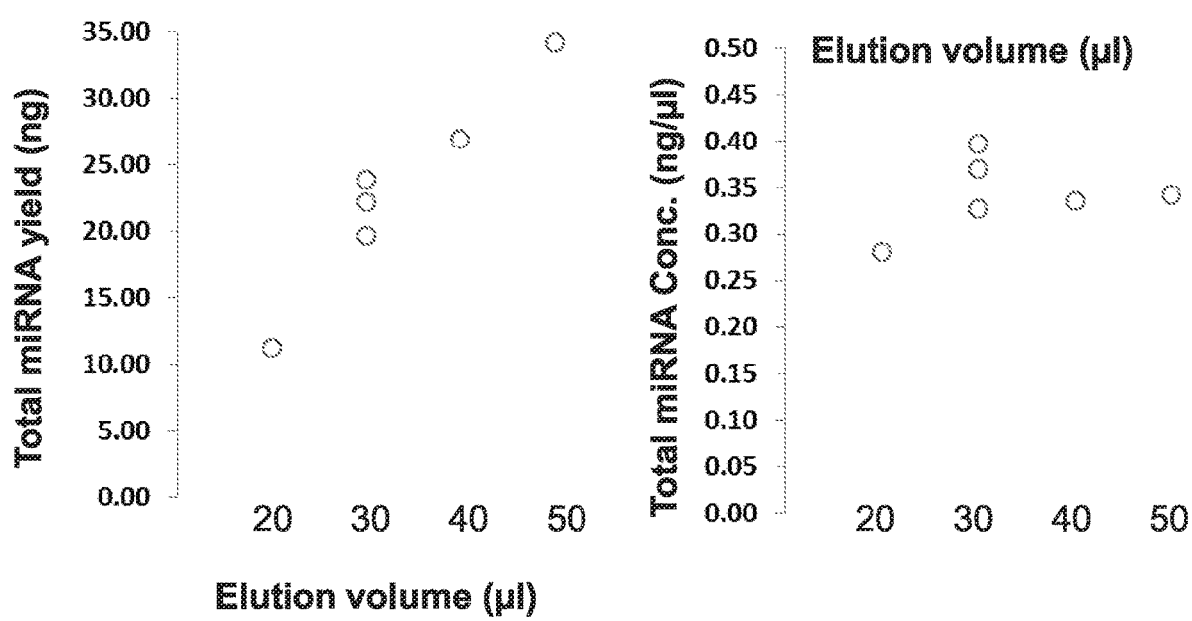
Figure 3 (Cont. 2)

Figure 4 (Cont. 1)
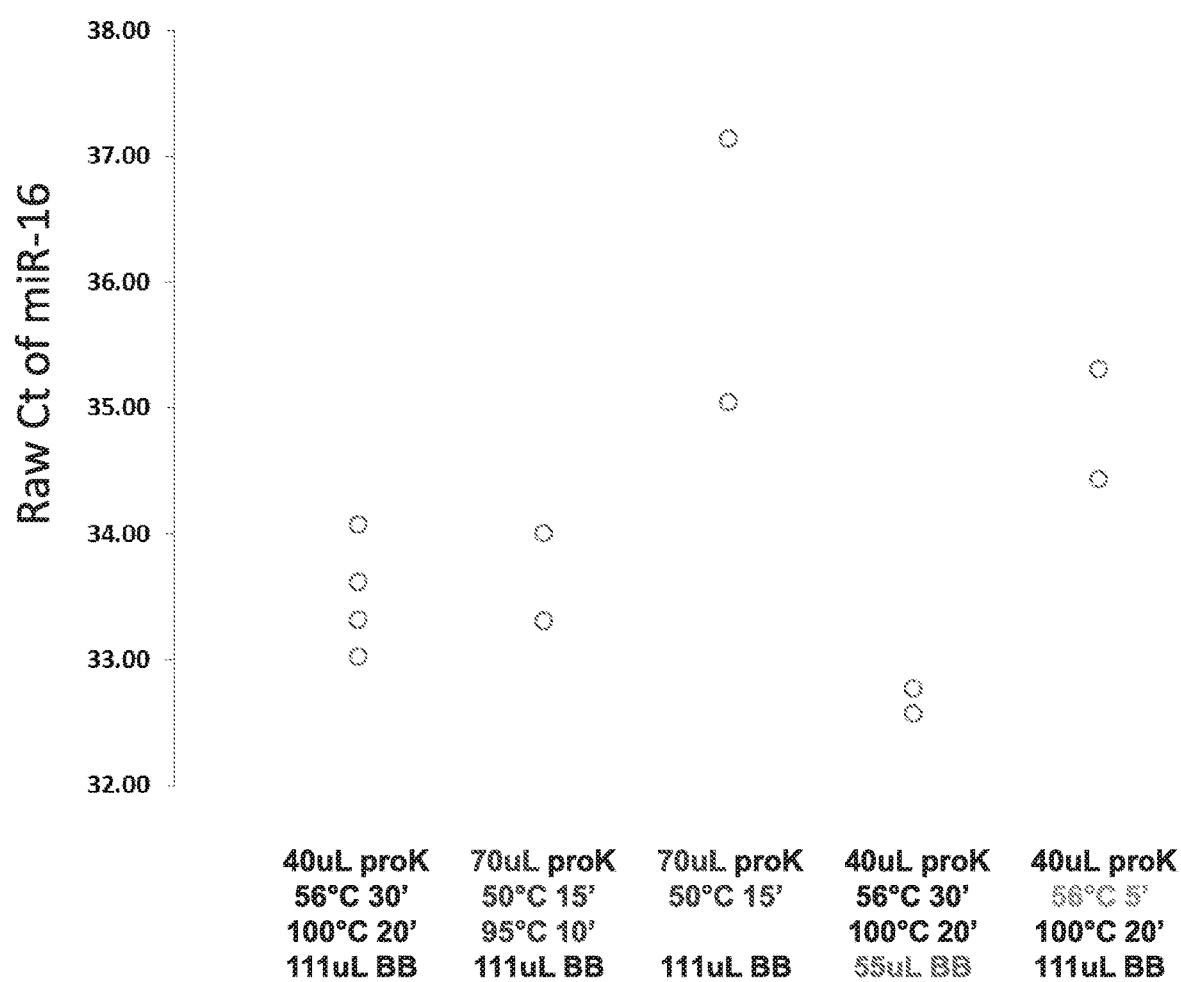

Figure 7 (Cont. 1)
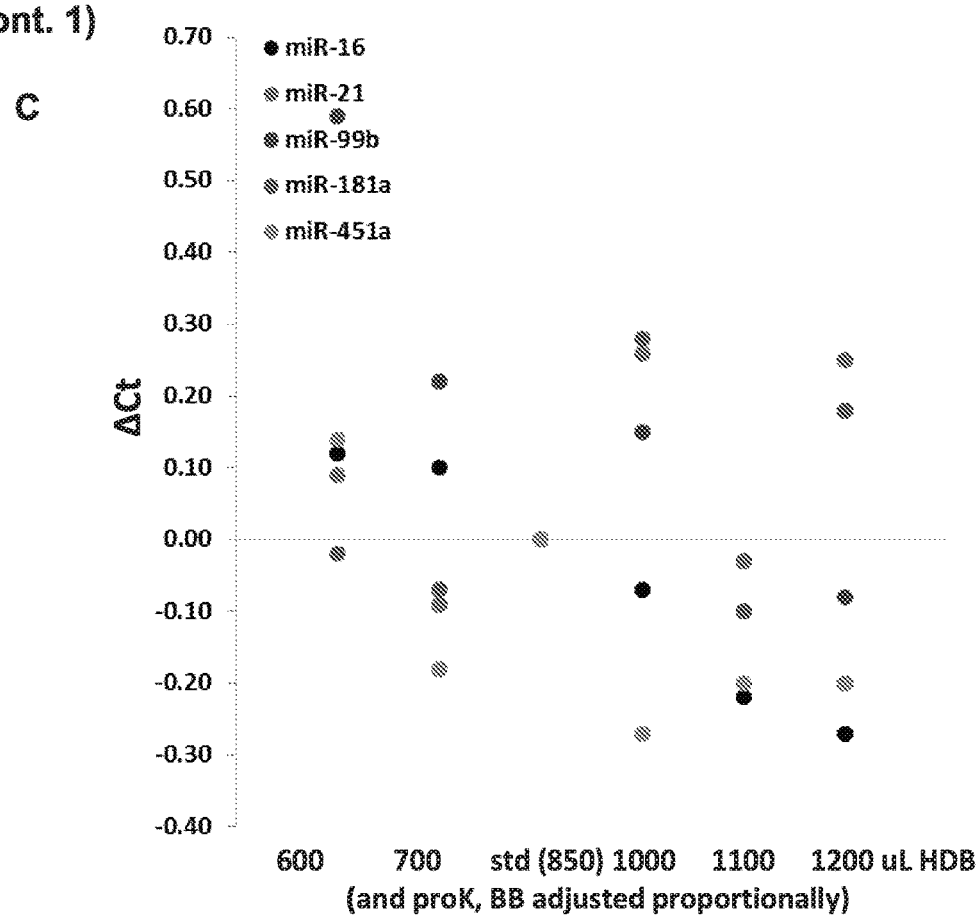
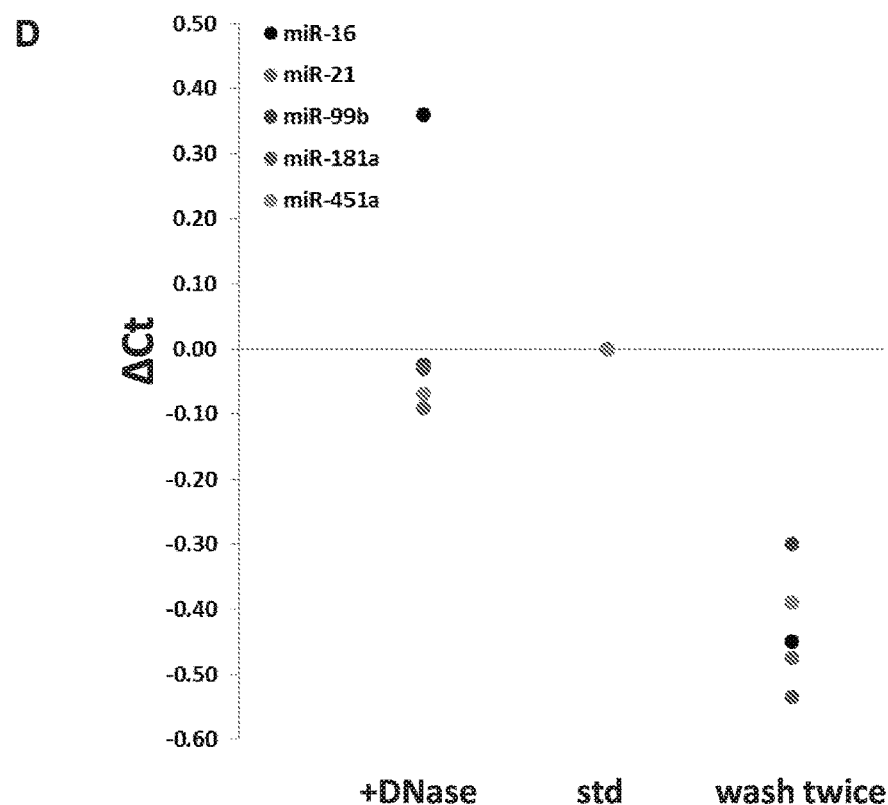

Figure 7 (Cont. 2)
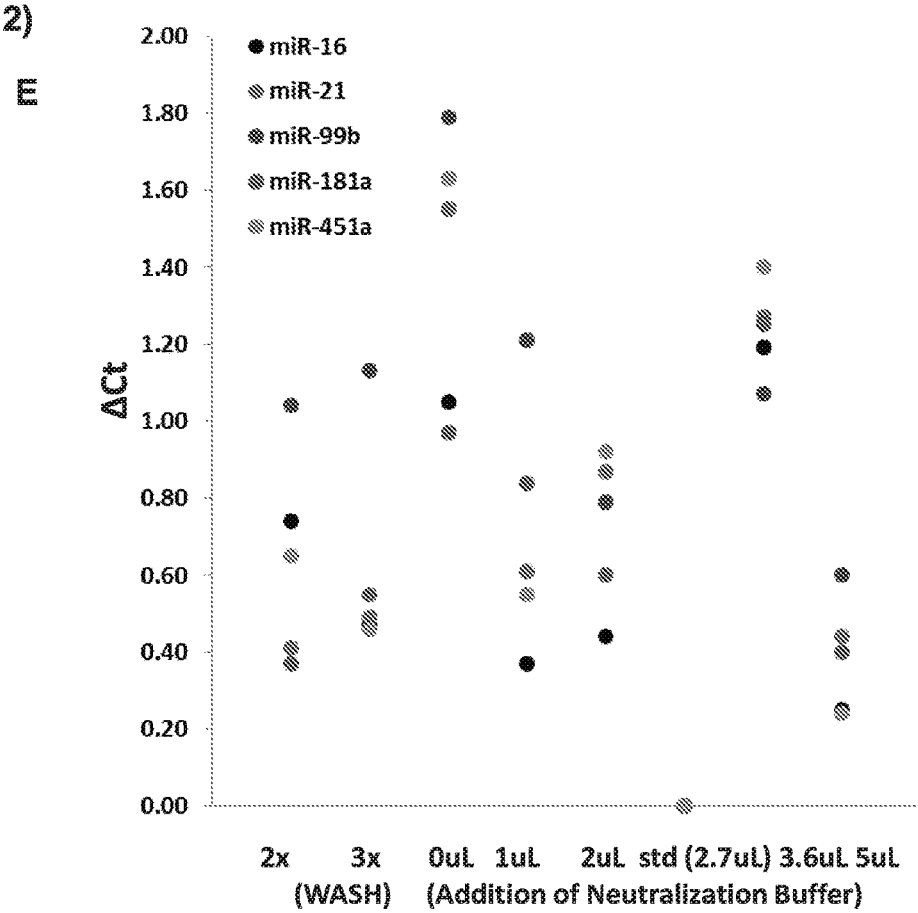
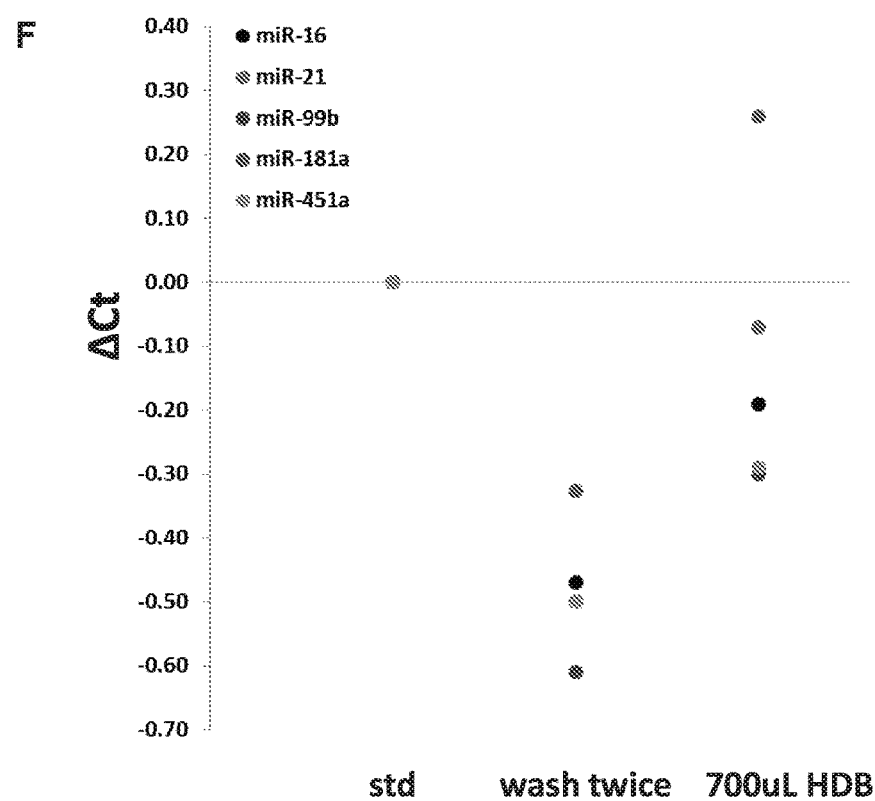

Figure 17 (Cont. 1)
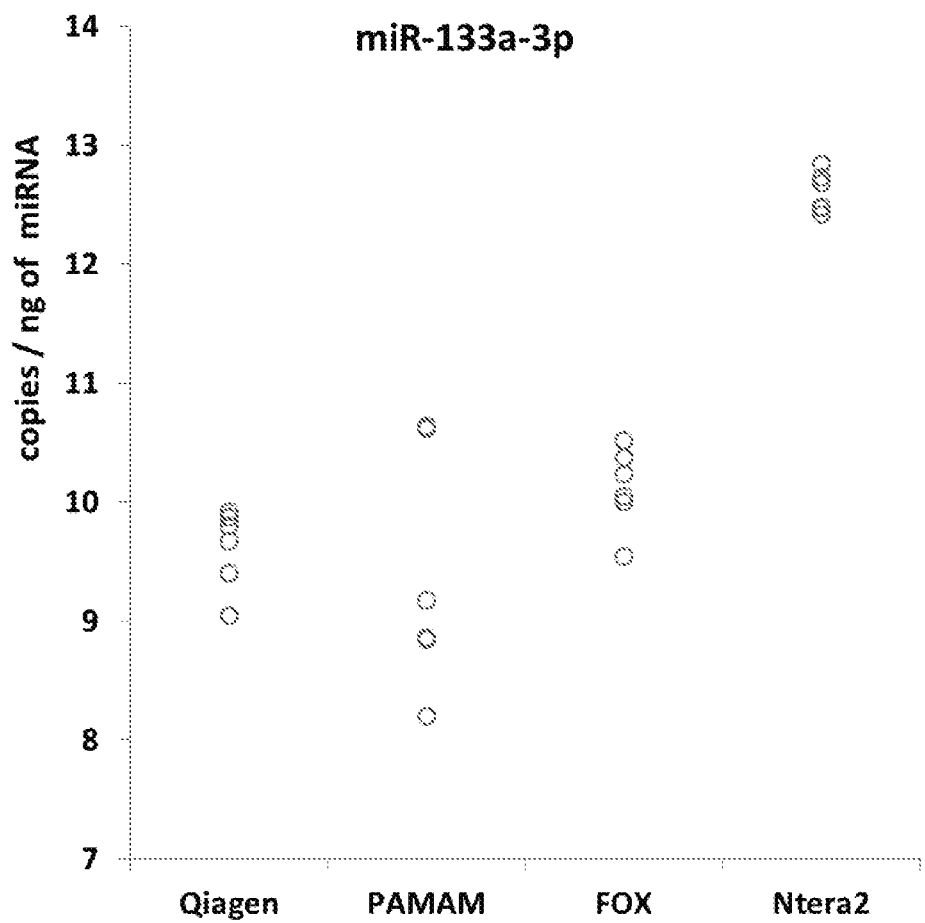
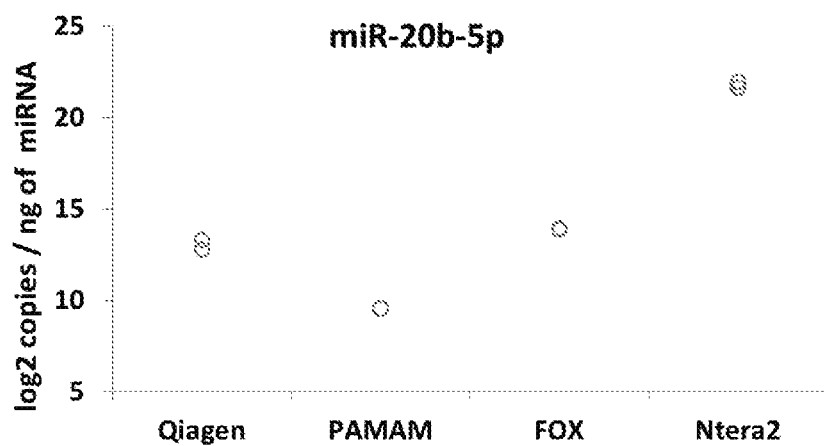

Figure 17 (Cont. 2)
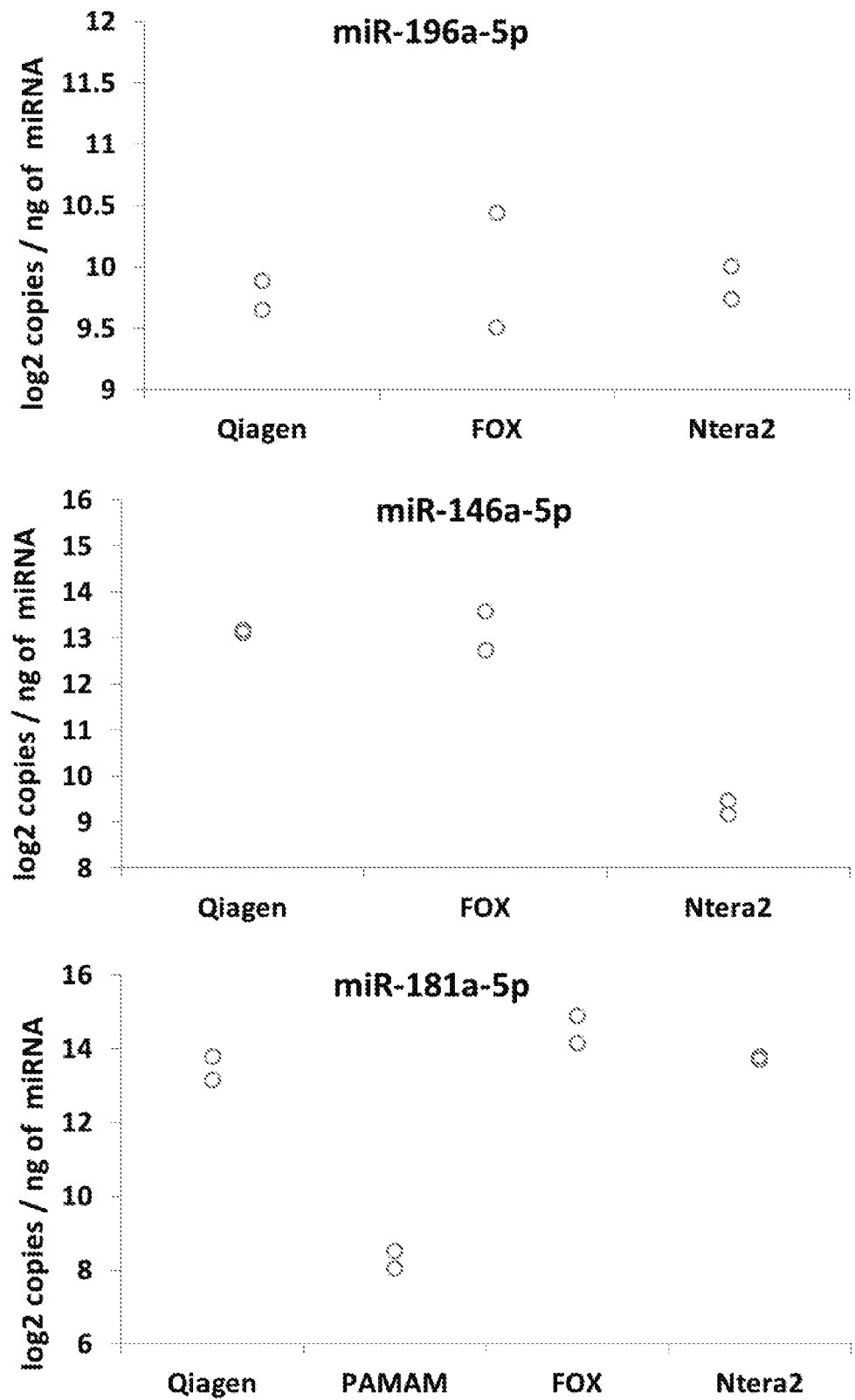

Figure 17 (Cont. 3)
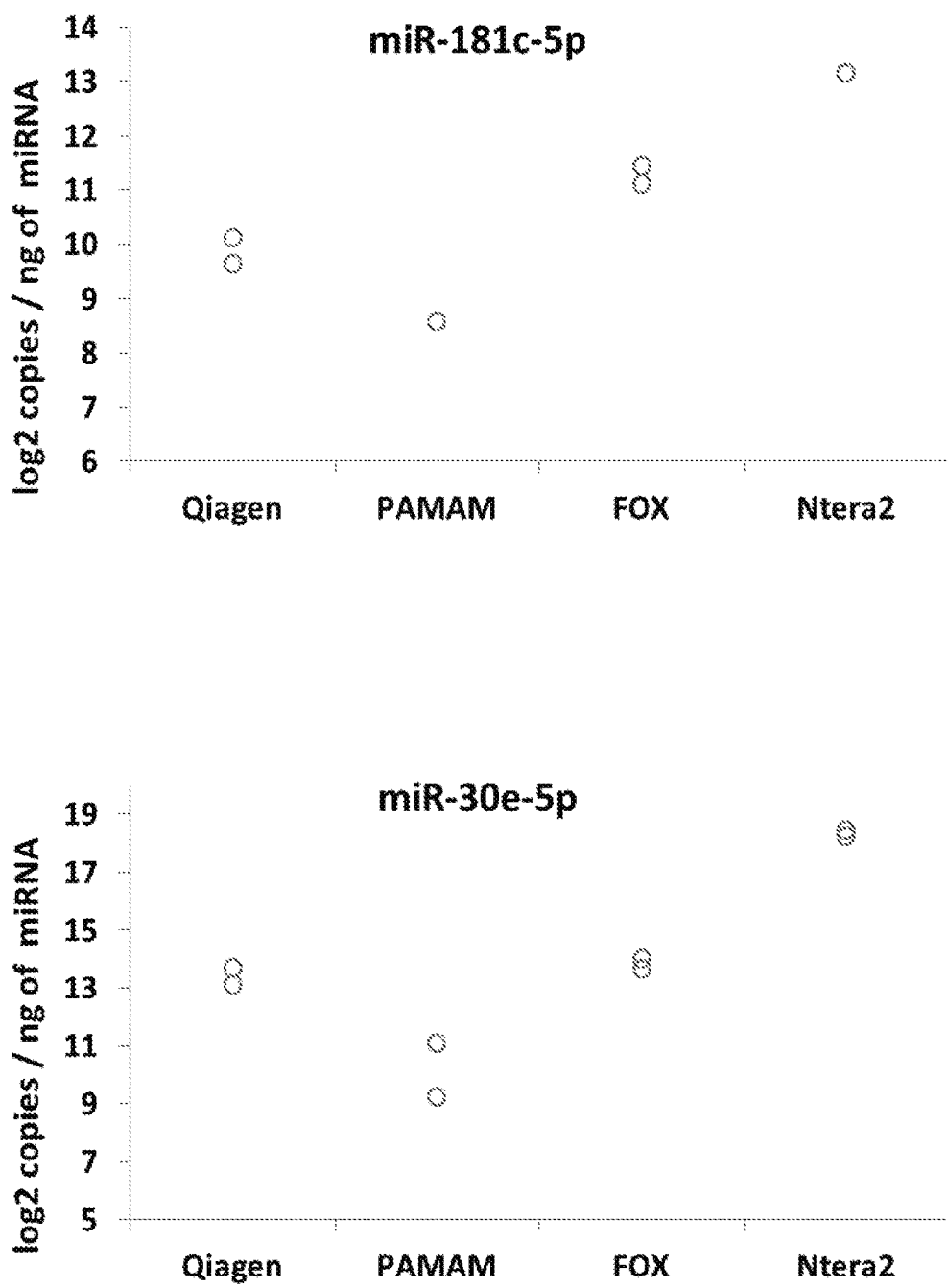

Figure 17 (Cont. 4)
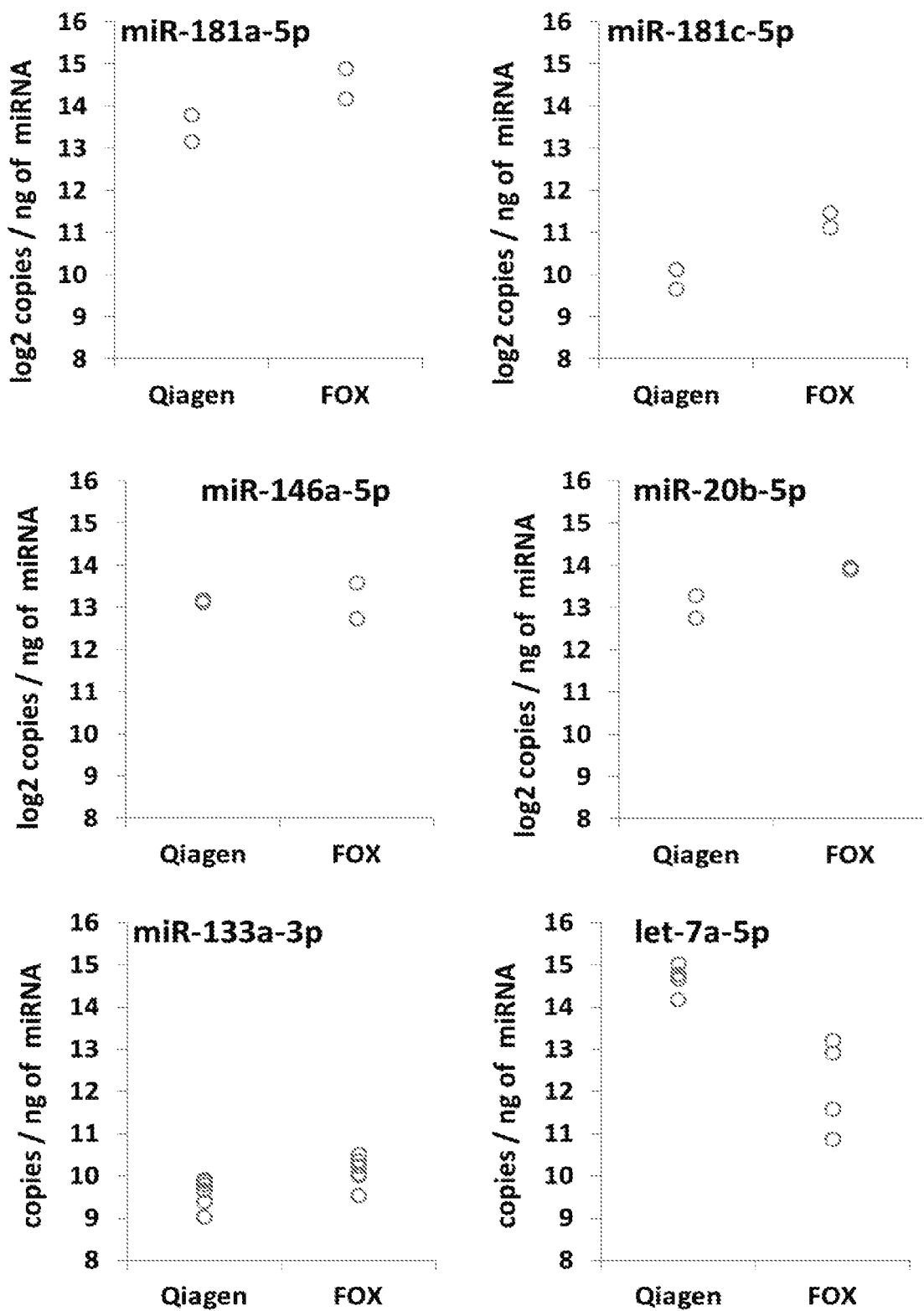

Figure 17 (Cont. 5)
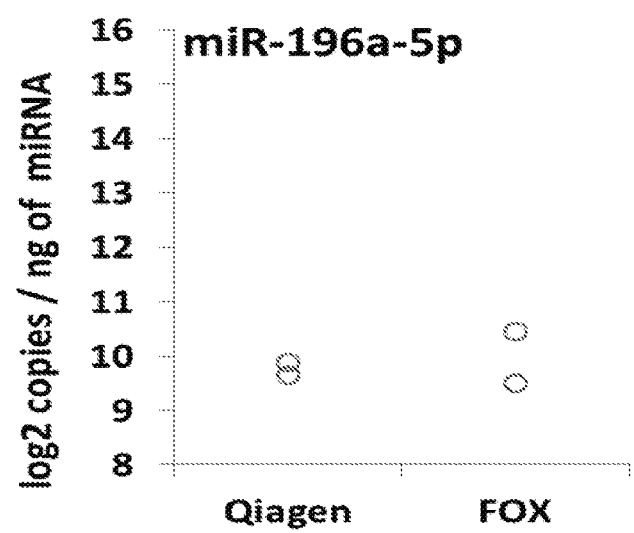
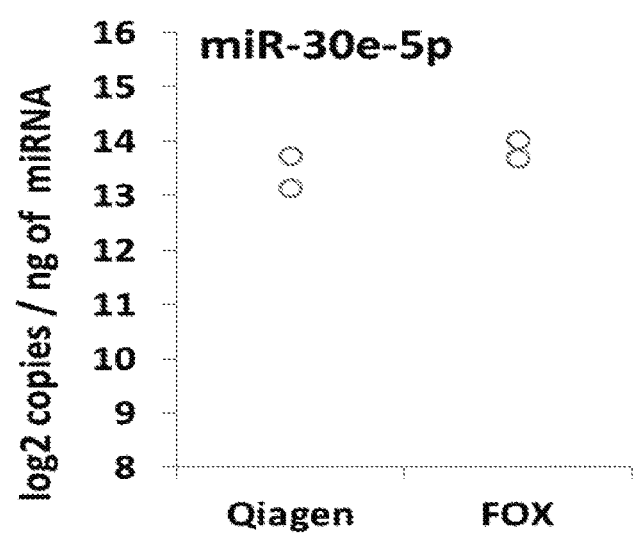
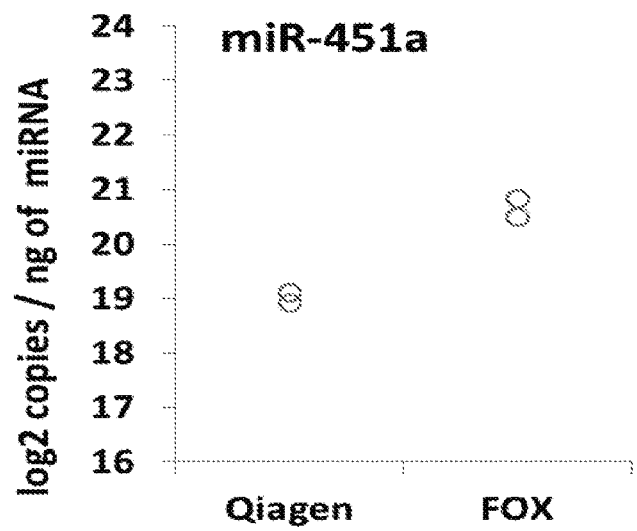

| Start with | 200 uL serum | |
|---|---|---|
| 1. | add 850uL HPV LBC Diluent | add 700uL HPV LBC Diluent |
| 2. | add 40uL proteinase K | add 60uL proteinase K |
| 3. | incubate at 56°C for 30min | incubate at 50°C for 10min |
| 4. | incubate at 100°C for 20min | incubate at 95°C for 10min |
| 5. | air cool to <40°C | ice/water cool 2min |
| 6. | transfer all sample to FOX extraction tube, allow 5min to dissolve | |
| 7. | N/A | pipet 10 times to mix |
| 8. | add 111uL Binding Buffer | add 47uL Binding Buffer |
| 9. | pipet 3 times to mix | pipet 10 times to mix |
| 10. | put on magnet, remove all liquid and bubbles | |
| 11. | add 950uL Wash Buffer | |
| 12. | pipet 3 times to mix | pipet 10 times to mix |
| 13. | put on magnet, remove all liquid and bubbles | |
| 14. | add 50uL 1X Elution Buffer | add 50uL 0.6X Elution Buffer |
| 15. | pipet 10 times to mix | pipet 20 times to mix |
| 16. | put on magnet | |
| 17. | transfer 50uL liquid to a new tube | transfer 45uL liquid to a new tube |
| 18. | add 50uL 1X Neutralization Buffer | add 2.7uL 11X Neutralization Buffer |
| Final Volume | 100uL | 47.7uL |
| Overall time | ~80min | ~35min |

US 11,674,133 B2

METHODS AND COMPOSITIONS FOR EXTRACTING NUCLEIC ACIDS USING FERRIC OXIDE PARTICLES

CROSS-REFERENCE TO RELATED APPLICATION

Pursuant to 35 U.S.C. § 119(e), this application claims priority to the filing date of U.S. Provisional Patent Application Ser. No. 62/558,074, filed Sep. 13, 2017; the disclosure of which application is incorporated herein by reference.

INTRODUCTION

Micro RNAs (miRNAs) are small (18-25 nucleotides in length) noncoding RNAs that can effectively reduce the expression of target mRNAs by binding to their 3' untranslated region (UTR). This activity occurs through the assembly of an RNA-induced silencing complex composed of catalytic enzymes, one of which is called Argonaut. If the homology between the miRNA sequence and the target 3'-UTR is incomplete, then this complex reduces expression by blocking translation. If, however, the homology is complete, then degradation of the target mRNA can be the end result. To date more than 2000 distinct human miRNAs capable of targeting thousands of genes have been identified. Each tissue has signature miRNAs that are expressed at consistent levels in a normal physiological state. However, in the case of diseased phenotypes these miRNAs are dysregulated. A variety of studies have shown the ability of individual miRNAs to regulate oncogene and tumor suppressor gene expression and others have shown that miRNA gene loss or mutation can contribute to tumor genesis.

SUMMARY

Methods and compositions for extracting nucleic acids such as microRNAs (miRNAs) from biological samples are provided. Aspects of the methods include contacting a biological sample with proteinase K followed by contact with ferric oxide particles under acidic conditions to induce binding between the ferric oxide particles and nucleic acids (e.g., miRNAs) within the sample. In some cases, the ferric oxide particles are provided as part of a dissolvable film, which releases the ferric oxide particles upon solvation. In some embodiments, after nucleic acids bind to the ferric oxide particles, the particles are magnetically separated from the sample and are contacted with an alkaline elution buffer to release the nucleic acids.

Embodiments of the provided methods are efficient and safe. For example, the methods of the disclosure do not require the use of chloroform or phenol and in some cases are completed in under thirty minutes. The subject methods and compositions are compatible with any convenient biological sample, including but not limited to: cultured cells, preserved (e.g., cross-linked/fixed) cells, whole blood, serum, plasma, formalin-fixed paraffin-embedded (FFPE) tissue samples, biopsies, organisms, including infectious disease organisms, e.g., bacteria and viruses, etc. In some cases, the extracted nucleic acids (e.g., miRNAs) can be used for a variety of downstream applications (e.g., diagnostics), where such applications may include quantitative analyses such as nucleic acid sequencing, e.g., via next generation sequencing (NGS), quantitative RT-PCR, strand displacement amplification (SDA), and microarray hybridization. In some cases, one or more abundant miRNAs are depleted from the sample, e.g., using ferric oxide particles that are conjugated to a nucleic acid probe that hybridizes with the abundant microRNA.

Aspects of embodiments of the methods include identifying biomolecules that bind to a target microRNA. For example, in some cases a biological sample is contacted with a population of ferric oxide particles that are conjugated to a nucleic acid probe that is complementary to a target microRNA, and the method includes identifying one or more biomolecule to which the target miRNA is bound.

Also provided are compositions and kits for performing the subject methods.

Embodiments of the invention meet the need for efficient methods for extracting nucleic acids, such as miRNAs, from biological samples. The compositions and methods provided herein facilitate efficient extraction of nucleic acids (e.g., miRNA) from a variety of biological sample types. The extracted nucleic acids can be used as diagnostic indicators and/or targets for therapy.

BRIEF DESCRIPTION OF THE FIGURES

FIG. 19 presents a table highlighting and comparing original FOX extraction protocol (left column) with improved FOX extraction protocol (right column).

DETAILED DESCRIPTION

Figure 1:
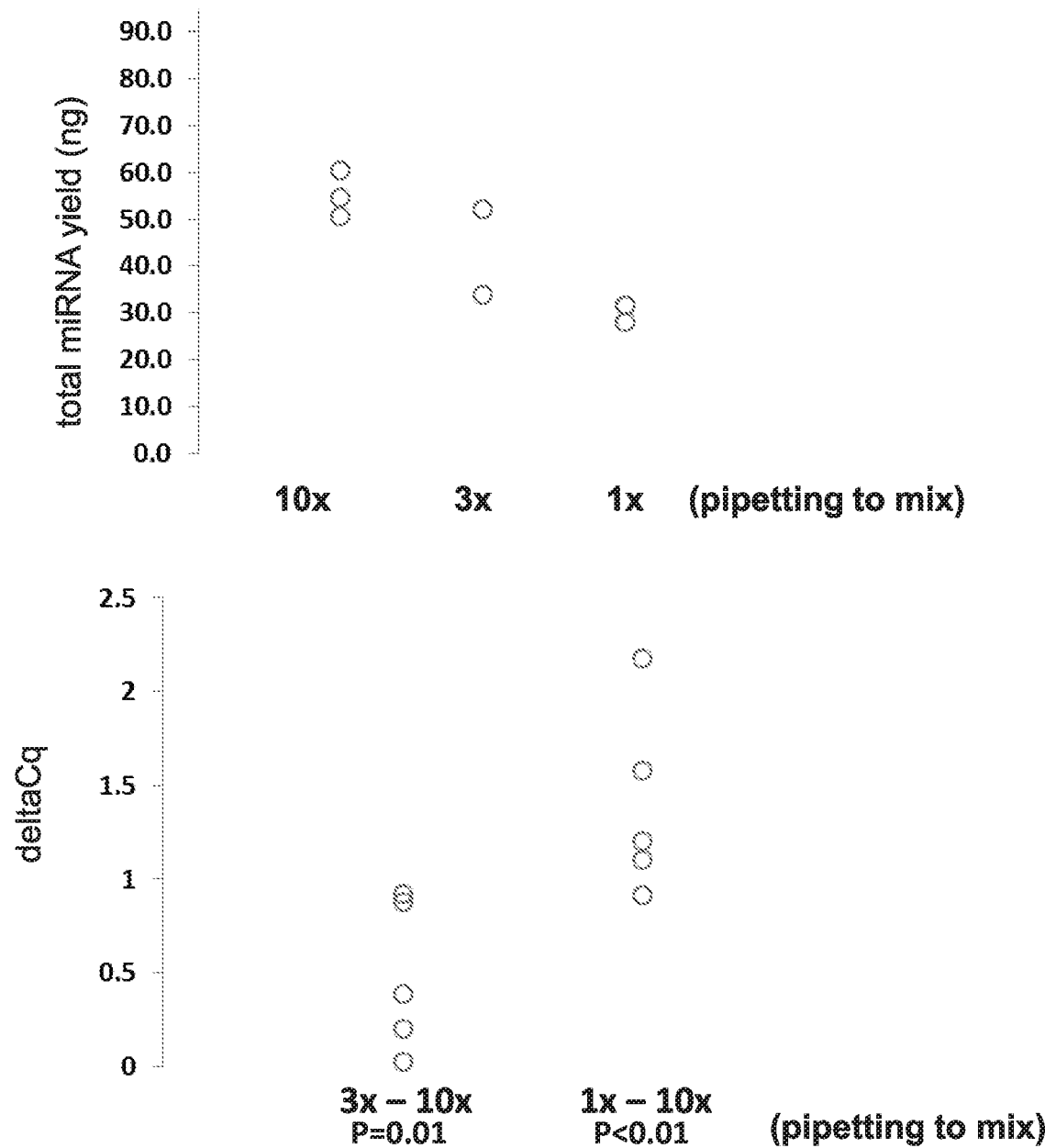
FIG. 1 depicts results obtained from evaluating whether the amount of mixing prior to elution affected yield of miRNA.
Figure 1:
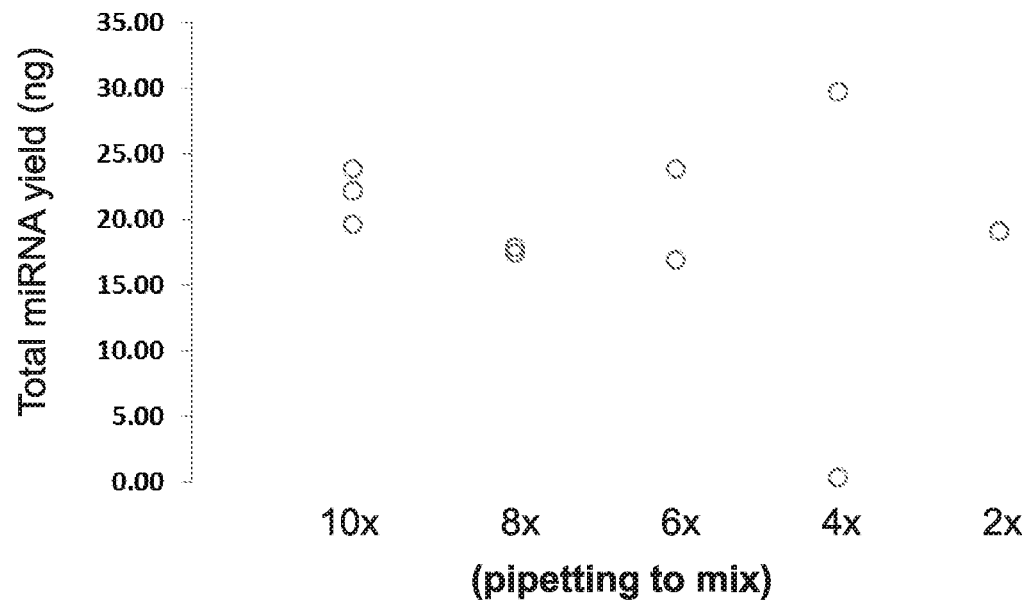
Figure 1:
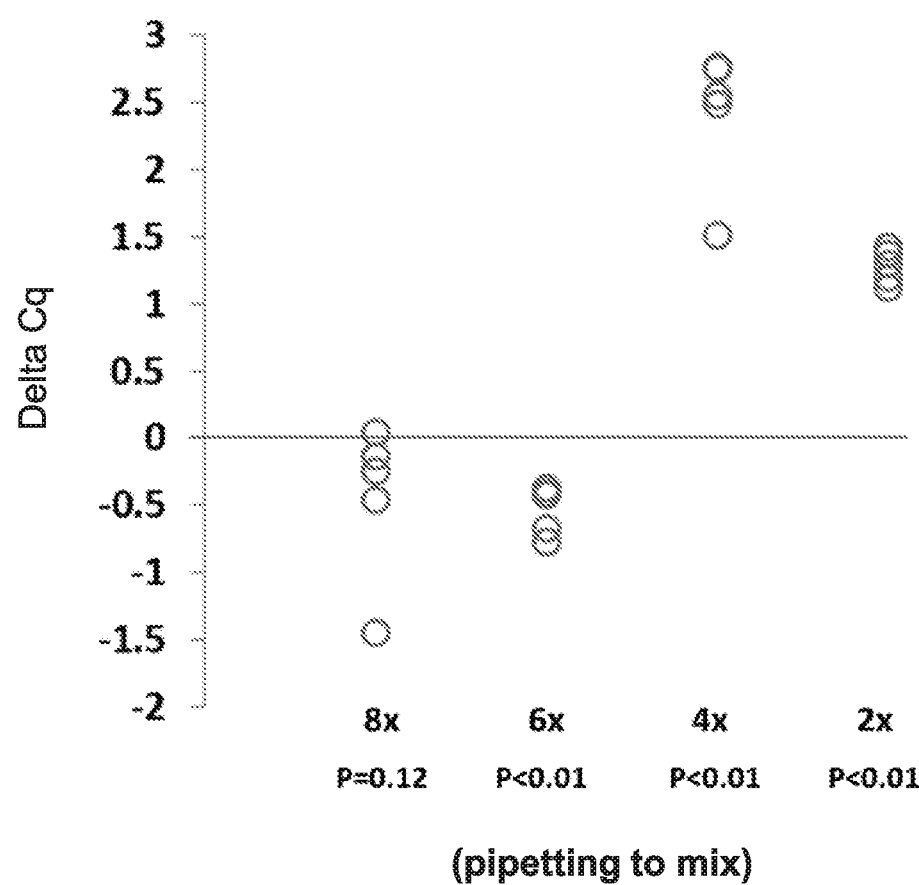

Methods and compositions for extracting nucleic acids such as microRNAs (miRNAs) from biological samples are provided. Aspects of the methods include contacting a biological sample with proteinase K followed by contact with ferric oxide particles under acidic conditions to induce binding between the ferric oxide particles and nucleic acids (e.g., miRNAs) of the sample. In some cases, the ferric oxide particles are provided as part of a dissolvable film, which releases the ferric oxide particles upon solvation. In some embodiments, after nucleic acids bind to the ferric oxide particles, the particles are magnetically separated from the sample and are contacted with an alkaline elution buffer to release the nucleic acids.

In some embodiments, methods for identifying biomolecules that bind to a target microRNA are provided. For example, in some cases a biological sample is contacted with a population of ferric oxide particles that are conjugated to a nucleic acid probe that is complementary to a target microRNA, and the method includes identifying one or more biomolecules to which the target miRNA is bound.

Also provided are compositions and kits for performing the subject methods.

Before embodiments of the present disclosure are described in greater detail, it is to be understood that this disclosure is not limited to particular embodiments described, as such may, of course, vary. The disclosure encompasses various alternatives, modifications, and equivalents, as will be appreciated by those of skill in the art. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

In determining whether a number is near to or approximately a specifically recited number, the near or approximating unrecited number may be a number which, in the context in which it is presented, provides the substantial equivalent of the specifically recited number.

It is noted that, as used herein and in the appended claims, the singular forms "a", "an", and "the" include plural referents unless the context clearly dictates otherwise. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which can be readily separated from or combined with the features of any of the other several embodiments without departing from the scope or spirit of the present disclosure. Any recited method can be carried out in the order of events recited or in any other order which is logically possible.

Any publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided may be different from the actual publication dates which may need to be independently confirmed.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, representative illustrative methods and materials are now described.

Methods and Compositions

Aspects of the disclosure include methods for extracting nucleic acids (e.g., microRNA, mRNA, DNA) from biological samples. In some cases the extracted nucleic acids are microRNAs (miRNAs). As such, aspects of the disclosure include methods for extracting microRNAs (miRNAs) from biological samples.

The term "biological sample" as used herein encompasses any sample of biological origin and encompasses samples such as whole blood, plasma, serum, aspirate, cerebrospinal fluid, urine, saliva, ascites fluid, tumoral fluid, a papanicolaou (pap) smear sample, a biological fluid, and also includes tissue obtained by surgical resection, tissue obtained by biopsy, cells in culture, cell supernatants, cell lysates, tissue samples, organs, bone marrow, and the like. A "biological sample" includes biological fluids and cells derived therefrom (e.g., cancerous cell, infected cell, etc.), e.g., a sample comprising polynucleotides that is obtained from such cells (e.g., a cell lysate or other cell extract comprising polynucleotides). The definition also includes microbial organisms, e.g., bacteria, viruses, etc., where in some instances the microbial organisms are infectious microbial organisms, e.g., that give rise to an infectious disease condition. The definition also includes samples that have been manipulated in any way after their procurement, such as by treatment with reagents such as fixation reagents, solubilization, enrichment for certain components, or labeling (e.g., non-covalent or covalent labeling with a label).

In some cases the biological sample is a cellular sample and in some cases the biological sample is acellular (does not include cells). The nucleic acids to be extracted can be within cells of a biological sample, and in some cases, the sample includes extracellular nucleic acids (e.g., in exosomes, in microvesicles, not encapsulated, cell free, and the like). Thus in some cases only extracellular nucleic acids are extracted (e.g., if a biological sample does not include cells and/or if the method does not include a step such as a cellular lysis step to expose intracellular nucleic acids). In some cases only intracellular nucleic acids are extracted (e.g., if the biological sample does not include extracellular nucleic acids). In some cases, both extracellular and intracellular nucleic acids are extracted.

Thus, in some embodiments, a method of the disclosure (i.e., a "subject method") does not include a step of lysing cells of the sample and in some cases a subject method does include a step of lysing cells of the sample. In some cases a subject method does not include a step of contacting cells of the sample with a solution that includes a detergent (e.g., to free nucleic acids from cells and/or from exosomes and microvesicles etc.). In some cases a subject method does include a step of contacting cells of the sample with a solution that includes a detergent (e.g., to free nucleic acids from cells and/or from exosomes and microvesicles etc.). Cellular lysis, when desired, can be performed using any convenient method (e.g., using a lysis buffer, contact with detergent, lysis without detergent such as using sonication and/or other physical means, and the like).

In some cases the nucleic acids of the biological sample are cross-linked. For example, in some cases the samples has previously been fixed (e.g., with formaldehyde). In some such cases, the biological sample is a fixed cellular sample (e.g., a sample that includes cells that were fixed in culture, a sample that includes cells that were fixed in vivo). In some cases the biological sample is a formalin-fixed paraffin-embedded (FFPE) tissue sample. In some cases the biological sample includes cells from an FFPE tissue sample.

The subject methods may be DNase compatible, and as such in some cases a subject method includes a step of contact with a DNase to remove DNA from the sample while leaving RNA, such as miRNA, intact. In some cases, one or more steps of a subject method is performed by a liquid handling robot. In some cases, all steps of a subject method are performed by a liquid handling robot. In some cases, the method (from contact with the protease, e.g., proteinase K, through elution) is completed in 45 minutes or less (e.g., 40 minutes or less, 35 minutes or less, 30 minutes or less).

Sample Diluent

In some cases a sample is diluted in a sample diluent, e.g., in some cases prior to contact with a protease (e.g., proteinase K) and in some cases after contact with a protease (e.g., proteinase K). The sample diluent can be any convenient buffer compatible with preserving nucleic acids. For example, in some cases, the sample diluent includes a buffering agent such as Tris (e.g., Tris HCl) (e.g., in some cases at a concentration between 200 mM-1.5M).

In some cases the sample diluent can be used as a lysis buffer. As such, in some cases the sample diluent includes one or more detergents (e.g., Triton X-100, Triton X-114, NP-40, BriJ-35, BriJ-58, Tween 20, Tween 80, Octyl glucoside, Octyl thioglucoside, SDS, CHAPS, CHAPSO, and the like). In some such cases, the detergent is at a concentration in a range of from 0.2% to 2% (e.g., 0.2-1.5%, 0.2-1%, 0.5-2%, 0.5-1.5%, or from 0.5-1%).

Any convenient volume (for the sample diluent) can be used and in some instances may be chosen in view of the amount of starting material. For example, when 200 μL of biological sample is used, the volume of sample diluent used can in some cases be in a range of from 500 to 1000 μL (e.g., from 500 to 900, 500 to 800, 500 to 750, 500 to 700, 600 to 1000, 600 to 900, 600 to 800, 600 to 750, 600 to 700, 650 to 1000, 650 to 900, 650 to 800, 650 to 750, or 650 to 700 μL). As another example, when 200 μL of biological sample is used, the volume of sample diluent used can in some cases be in a range of from 600 to 800 μL (e.g., from 650 to 750 μL). As another example, when 200 μL of biological sample is used, the volume of sample diluent used is about 600, 650, 700, 750, 800, or 850 μL. In some such cases the volume of sample diluent used is about 700 μL. In some cases the volume of sample diluent used is about 850 μL. In some cases the volume of sample diluent used is about 750 μL. In some cases the volume of sample diluent used is about 800 μL.

As noted elsewhere in the disclosure volumes presented as specific values (e.g., "x" μL) throughout the figures and text of the disclosure (for all reagents used in the subject methods—not just those discussed in relation to the volume of sample diluent), can be scaled based on the starting volume of the biological sample. As an illustrative example, in some cases the amount of sample diluent used is in a range of from 2.5 to 5 volumes (relative to the starting volume of the biological sample) (e.g., from 2.5 to 4.5, 2.5 to 4, 2.5 to 3.75, 2.5 to 3.5, 2.5 to 3, 3 to 5, 3 to 4.5, 3 to 4, 3 to 3.75, 3 to 3.5, 3.5 to 5, 3.5 to 4.5, 3.5 to 4, or 3.25 to 3.75 volumes). In some cases the amount of sample diluent used is in a range of from 3.25 to 3.75 volumes (relative to the starting volume of the biological sample). In some cases the amount of sample diluent used is about 3.5 volumes (relative to the starting volume of the biological sample). In some cases the amount of sample diluent used is about 4.25 volumes (relative to the starting volume of the biological sample). In some cases the amount of sample diluent used is about 4 volumes (relative to the starting volume of the biological sample).

In some cases, the sample diluent is alkaline. For example, in some cases the sample diluent has a pH in a range of from 8-12.5 (e.g., 8-12, 8-11, 8-11.5, 8-10.5, 8-10, 8-9.5, 8-9, 8.5-12.5, 8.5-12, 8.5-11.5, 8.5-11, 8.5-10.5, 8.5-10, 8.5-9.5, 9-12.5, 9-12, 9-11.5, 9-11, 9-10.5, or 9-10). In some cases the sample diluent includes an antimicrobial agent (e.g., Proclin).

One illustrative example of a suitable sample diluent is one that includes 599 mM Tris-HCl, 373 mM Tris Base, 243 mM NaCl, 0.83% Triton X-100, and 0.03% Proclin.

Proteinase K

As noted above, in some embodiments a biological sample is contacted with Proteinase K. However, any convenient protease (protein-digesting enzyme) can be used. In some cases the protease can be any non-specific protease such as any non-specific serine protease (e.g., subtilisin or other other subtilisin-type proteases).

Contacting the sample with a protease (e.g., proteinase K) degrades proteins present in the sample, and can be performed at a variety of temperatures and over a variety of times. In some embodiments, contact with a protease (e.g., proteinase K) takes place at a temperature in a range of from 45° C. to 56° C. (e.g., from 45 to 55, 45 to 54, 45 to 53, 45 to 52, 45 to 51, 45 to 50, 47 to 56, 47 to 55, 47 to 54, 47 to 53, 47 to 52, 47 to 51, 47 to 50, 48 to 56, 48 to 55, 48 to 54, 48 to 53, 48 to 52, 48 to 51, 48 to 50, 49 to 56, 49 to 55, 49 to 54, 49 to 53, 49 to 52, or 49 to 51° C.). In some cases, contact with a protease (e.g., proteinase K) takes place at a temperature in a range of from 45° C. to 55° C. (e.g., from 45 to 54, 45 to 53, 45 to 52, 45 to 51, 45 to 50, 47 to 55, 47 to 54, 47 to 53, 47 to 52, 47 to 51, 47 to 50, 48 to 55, 48 to 54, 48 to 53, 48 to 52, 48 to 51, 48 to 50, 49 to 55, 49 to 54, 49 to 53, 49 to 52, or 49 to 51° C.). In some cases the contact with a protease (e.g., proteinase K) takes place at a temperature in a range of from 47° C. to 53° C. (e.g., from 47 to 52, 47 to 51, 47 to 50, 48 to 53, 48 to 52, 48 to 51, 49 to 53, 49 to 52, or 49 to 51° C.). In some cases the contact with a protease (e.g., proteinase K) takes place at a temperature in a range of from 49° C. to 51° C. (e.g., 50° C.).

In some embodiments, contact with a protease (e.g., proteinase K) takes place for a period of time in a range of from 8 to 40 minutes (e.g., from 8 to 35, 8 to 30, 8 to 25, 8 to 20, 8 to 18, 8 to 15, 8 to 12, 10 to 40, 10 to 35, 10 to 30, 10 to 25, 10 to 20, 10 to 18, 10 to 15, 10 to 12, 15 to 40, 15 to 35, 15 to 30, 15 to 25, 15 to 20, 15 to 18, 20 to 40, 20 to 35, 20 to 30, 25 to 40, 25 to 35, 25 to 30, or 28 to 32 minutes). In some cases contact with a protease (e.g., proteinase K) takes place for a period of time in a range of from 20 to 40 minutes (e.g., from 20 to 35, 20 to 30, 25 to 40, 25 to 35, 25 to 32, 25 to 30, 28 to 40, 28 to 35, or 28 to 32 minutes). In some cases contact with a protease (e.g., proteinase K) takes place for about 10 minutes. In some cases contact with a protease (e.g., proteinase K) takes place for about 15 minutes. In some cases contact with a protease (e.g., proteinase K) takes place for about 20 minutes. In some cases contact with a protease (e.g., proteinase K) takes place for about 25 minutes. In some cases contact with a protease (e.g., proteinase K) takes place for about 30 minutes.

In some embodiments, contact with a protease (e.g., proteinase K) takes place at a temperature in a range of from 47° C. to 53° C. and for a period of time in a range of from 8 to 40 minutes (e.g., from 8 to 15, 8 to 12, 25 to 40, 25 to 35, 25 to 32, 28 to 40, 28 to 25, or 28 to 32 minutes). In some embodiments, contact with a protease (e.g., proteinase K) takes place at a temperature in a range of from 47° C. to 53° C. and for about 30 minutes. In some embodiments, contact with a protease (e.g., proteinase K) takes place at a temperature in a range of from 47° C. to 53° C. and for about 10 minutes. In some cases contact with a protease (e.g., proteinase K) takes place at a temperature in a range of from 48° C. to 52° C. and for a period of time in a range of from 10 to 30 minutes. In some cases contact with a protease (e.g., proteinase K) takes place at a temperature in a range of from 47° C. to 53° C. (e.g., from 48 to 52 or 49 to 51° C., or at 50° C.) and for a period of time in a range of from 20 to 35 minutes (e.g., from 25 to 35, 28 to 32, or 29 to 31 minutes or for 30 minutes). In some embodiments, contact with a protease (e.g., proteinase K) takes place at a temperature in a range of from 48° C. to 52° C. and for about 30 minutes. In some embodiments, contact with a protease (e.g., proteinase K) takes place at a temperature in a range of from 48° C. to 52° C. and for about 10 minutes.

In some embodiments, the protease (e.g., proteinase K) is used at a concentration in a range of from 750 to 1600 μg/mL (e.g., from 750 to 1500, 750 to 1400, 750 to 1350, 800 to 1600, 800 to 1500, 800 to 1400, 800 to 1350, 900 to 1600, 900 to 1500, 900 to 1400, 900 to 1350, 1000 to 1600, 1000 to 1500, 1000 to 1400, 1000 to 1350, 1100 to 1600, 1100 to 1500, 1100 to 1400, 1100 to 1350, 1200 to 1600, 1200 to 1500, 1200 to 1400, or from 1200 to 1350, μg/mL). In some cases, the protease (e.g., proteinase K) is used at a concentration in a range of from 1100 to 1400 μg/ml (e.g., 1250 μg/ml). In some cases, the protease (e.g., proteinase K) is used at a concentration of about 1250 μg/mL As an illustrative example (e.g., see right side of FIG. 19), if a stock concentration of proteinase K has a concentration of 20 mg/mL, and 60 μL of the stock solution is added to 900 μL (e.g., 200 μL of sample plus 700 μL of a diluent), then the proteinase K would be used at a concentration of 1.3 mg/mL.

In some embodiments, the protease (e.g., proteinase K) is used at a concentration in a range of from 22 to 48 mAU/mL (e.g., from 25 to 45, 25 to 40, 30 to 48, 30 to 40, 35 to 48, 35 to 45, or from 35 to 40 mAU/mL). In some cases, the protease (e.g., proteinase K) is used at a concentration in a range of from 35 to 40 mAU/mL (e.g., 37.5 mAU/mL).

Any convenient volume (for the protease) can be used and this will likely depend on the amount of starting material. For example, when 200 μL of biological sample is used, the volume of protease (e.g., proteinase K) used can in some cases be in a range of from 45 to 80 μL (e.g., from 45 to 75, 45 to 70, 45 to 65, 45 to 62, 50 to 80, 50 to 75, 50 to 70, 50 to 65, 50 to 62, 55 to 80, 55 to 75, 55 to 70, 55 to 65, 55 to 62, 58 to 80, 58 to 75, 58 to 70, 58 to 65, or 58 to 62 μL). As another example, in some such cases the volume of protease (e.g., proteinase K) used is about 45, 50, 55, 60, 65, 70, or 80 μL. In some cases the volume of protease (e.g., proteinase K) used is about 45 μL. In some cases the volume of protease (e.g., proteinase K) used is about 50 μL. In some cases the volume of protease (e.g., proteinase K) used about 55 μL. In some cases the volume of protease (e.g., proteinase K) used about 60 μL. In some cases the volume of protease (e.g., proteinase K) used about 70 μL.

As noted elsewhere in the disclosure volumes presented as specific values (e.g., "x" μL) throughout the figures and text of the disclosure (for all reagents used in the subject methods—not just those discussed in relation to the volume of protease), can be scaled based on the starting volume of the biological sample. As an illustrative example, in some cases the amount of protease (e.g., proteinase K) used is in a range of from 0.225 to 0.4 volumes (relative to the starting volume of the biological sample) (e.g., from 0.225 to 0.375, 0.225 to 0.35, 0.225 to 0.325, 0.225 to 0.31, 0.25 to 0.4, 0.25 to 0.375, 0.25 to 0.35, 0.25 to 0.325, 0.25 to 0.31, 0.275 to 0.4, 0.275 to 0.375, 0.275 to 0.35, 0.275 to 0.325, 0.275 to 0.31, 0.29 to 0.4, 0.29 to 0.375, 0.29 to 0.35, 0.29 to 0.325, or 0.29 to 0.31 volumes). In some cases the amount of protease (e.g., proteinase K) used is about 0.225, 0.25, 0.275, 0.29, 0.3, 0.31, 0.325, 0.35, 0.375, or 0.4 volumes (relative to the starting volume of the biological sample). In some cases the amount of protease (e.g., proteinase K) used is about 0.15 volumes (relative to the starting volume of the biological sample). In some cases the amount of protease (e.g., proteinase K) used is about 0.25 volumes (relative to the starting volume of the biological sample). In some cases the amount of protease (e.g., proteinase K) used is about 0.275 volumes (relative to the starting volume of the biological sample). In some cases the amount of protease (e.g., proteinase K) used is about 0.3 volumes (relative to the starting volume of the biological sample). In some cases the amount of protease (e.g., proteinase K) used is about 0.325 volumes (relative to the starting volume of the biological sample). In some cases the amount of protease (e.g., proteinase K) used is about 0.35 volumes (relative to the starting volume of the biological sample).

In some cases, denaturation of the protease (e.g., proteinase K), e.g., via heating at 95° C. to 100° C.) is beneficial. In some such cases, a denaturation step can be used after contacting the sample with proteinase K, and prior to contact with the ferric oxide particles. If heat (e.g., boiling) is used for denaturation, too high of a temperature can in some cases be detrimental. For example, in some cases, heating is used for denaturation, and the temperate is below 114° C. (e.g., below 110° C. or below 105° C.). In some cases, heating is used for denaturation, and the temperate for denaturation is in a range of from 90-113° C. (e.g., in a range of from 90-110° C., 90-105° C., 90-100° C., 92-113° C., 92-110° C., 92-105° C., 92-100° C., 92-98° C., 95-113° C., 95-110° C., 95-105° C., or 95-100° C.). In some cases, the denaturation step (e.g., heating) takes place for 5 to 30 minutes (e.g., from 5 to 25, 5 to 20, 5 to 15, 5 to 12, 7 to 13, 8 to 12, 9 to 11, 7 to 30, 7 to 25, 7 to 20, 7 to 15, 7 to 12, 8 to 30, 8 to 25, 8 to 20, or 8 to 15 minutes). In some cases, denaturation is at a temperature in a range of from 92-98° C. and takes place for 8 to 12 minutes.

After a denaturation step, the sample can be cooled (e.g., to less than 40° C.). In some cases cooling takes place in the air (e.g., at room temperature). In some cases cooling take place on ice and/or in water (e.g., for a period of time in a range of from 1-20 minutes, e.g., from 1-15 minutes, 1-10 minutes, 1-5 minutes, 2-20 minutes, 2-15 minutes, 2-10 minutes, 2-5 minutes, or for 2 minutes). In some cases cooling take place on ice and/or in water for at least 1 minute (e.g., at least 2 minutes).

Binding Nucleic Acids with Ferric Oxide Particles

In some embodiments, after the biological sample is contacted with a protease (e.g., proteinase K), the sample is then contacted with ferric oxide (FOX) particles under acidic conditions to induce binding between the ferric oxide particles and nucleic acids (e.g., miRNAs) of the sample. As noted above, the term "ferric oxide particles" is used herein to encompass all forms of iron oxide particles (e.g., ferric hydroxide particles, ferrosoferric oxide particles, and the like). The contacting is performed under acidic conditions because at acidic pH the FOX particles become positively charged and bind to the negatively charged nucleic acids (elution is later performed under basic/alkaline conditions because at basic pH the FOX particles become negatively charged and the negatively charged nucleic acids are released into solution from the FOX particles).

In some cases the 'acidic conditions' are achieved by adding an acidic binding buffer. In some such cases contact between the sample and the FOX particles occurs prior to adding an acidic binding buffer. For example, in some cases, the protease (e.g., proteinase K)-contacted sample is contacted with the FOX particles. In some such cases, the FOX particles are part of a dissolvable film and sample is mixed with the FOX particles prior to contact with the acidic binding buffer.

In some embodiments, mixing of the FOX particles with the sample (and in some cases this includes solvation of the dissolvable film) can be accomplished by pipetting. In some such cases the sample is pipetted 3 or more times prior to adding binding buffer (e.g., 4 or more, 5 or more, 6 or more, 7 or more, 8 or more, 9 or more, or 10 or more times). In some cases the sample is pipetted about 10 times prior to adding binding buffer. In some such cases the sample is pipetted 3 or more times after adding the acidic binding buffer (e.g., 4 or more, 5 or more, 6 or more, 7 or more, 8 or more, 9 or more, or 10 or more times). In some cases the sample is pipetted about 10 times after adding the acidic binding buffer. In some such cases the sample is pipetted 3 or more times before and after adding the acidic binding buffer (e.g., 4 or more, 5 or more, 6 or more, 7 or more, 8 or more, 9 or more, or 10 or more times). In some cases the sample is pipetted about 10 times before and after adding the acidic binding buffer.

The acidic binding buffer can be any convenient buffer (e.g., one that includes sodium phosphate and/or potassium phosphate) and in some cases acid such as sulfuric acid can be used to bring the pH of the buffer into a desired range. As an illustrative example, the acidic binding buffer can in some cases include sodium phosphate, monobasic (e.g., 0.5 M) and sulfuric acid (e.g., 3.75 M).

In some embodiments, the pH of the acidic binding buffer will be in a range of from 1.2 to 3 (e.g., 1.2 to 2.8, 1.2 to 2.6, 1.2 to 2.4, 1.2 to 2.2, 1.2 to 2, 1.3 to 3, 1.3 to 2.8, 1.3 to 2.6, 1.3 to 2.4, 1.3 to 2.2, 1.3 to 2, 1.4 to 3, 1.4 to 2.8, 1.4 to 2.6, 1.4 to 2.4, 1.4 to 2.2, 1.4 to 2, 1.5 to 3, 1.5 to 2.8, 1.5 to 2.6, 1.5 to 2.4, 1.5 to 2.2, or 1.5 to 2). In some cases the pH of the acidic binding buffer will be in a range of from 1.5 to 2.

Any convenient volume (for the acidic binding buffer) can be used and this will likely depend on the amount of starting material. For example, when 200 µL of biological sample is used, the volume of acidic binding buffer used can in some cases be in a range of from 40 to 120 µL (e.g., from 40 to 115, 40 to 100, 40 to 90, 40 to 80, 40 to 70, 40 to 60, 40 to 55, 40 to 52, 40 to 50, 45 to 115, 45 to 100, 45 to 90, 45 to 80, 45 to 70, 45 to 60, 45 to 55, 45 to 52, 45 to 50, 50 to 115, 50 to 100, 50 to 90, 50 to 80, 50 to 70, or 50 to 60 µL). As another example, in some such cases the volume of acidic binding buffer used is about 45, 47, 50 or 55 µL. In some cases the volume of acidic binding buffer used is about 47 µL. In some cases the volume of acidic binding buffer used is about 55 µL.

As noted elsewhere in the disclosure volumes presented as specific values (e.g., "x" µL) throughout the figures and text of the disclosure (for all reagents used in the subject methods—not just those discussed in relation to the volume of acidic binding buffer), can be scaled based on the starting volume of the biological sample. As an illustrative example, in some cases the amount of acidic binding buffer used is in a range of from 0.2 to 0.6 volumes (relative to the starting volume of the biological sample) (e.g., from 0.2 to 0.5, 0.2 to 0.4, 0.2 to 0.3, 0.2 to 0.25, 0.2 to 0.235, 0.225 to 0.5, 0.225 to 0.4, 0.225 to 0.3, 0.225 to 0.285, 0.225 to 0.25, or 0.225 to 0.235 volumes). In some cases the amount of acidic binding buffer used is about 0.225, 0.235, 0.25, or 0.275 volumes (relative to the starting volume of the biological sample). In some cases the amount of acidic binding buffer used is about 0.225 volumes (relative to the starting volume of the biological sample). In some cases the amount of acidic binding buffer used is about 0.235 volumes (relative to the starting volume of the biological sample). In some cases the amount of acidic binding buffer used is about 0.275 volumes (relative to the starting volume of the biological sample).

In some cases, magnetically-responsive particles (ferric oxide particles) of the disclosure are provided/used as part of a dissolvable film that dissolves to release the FOX particles to bind to the nucleic acids of the sample. The term "ferric oxide particles" is used herein to encompass all forms of iron oxide particles (e.g., ferric hydroxide particles, ferrosoferric oxide particles, and the like). Films suitable for use in conjunction with the present disclosure can be made by techniques familiar to those of in the art, such as the technique described in U.S. Pat. No. 6,419,903, which is hereby incorporated by reference in its entirety, e.g., for teachings related to techniques for making films. Also see U.S. Pat. No. 9,267,167, which is hereby incorporated by reference in its entirety, e.g., for its teachings related to "magnetically-responsive particles" (e.g., iron oxide particles) and dissolvable films.

In some cases, the dissolvable film is formed from a material including one or more of: hydroxyalkylmethyl cellulose; carboxymethyl cellulose; carboxylic hydroxyalkyl ester monomer; ethoxylated hydroxyalkyl(meth)acrylate; propoxylated hydroxyalkyl(meth)acrylate; polyethylene glycol (PEG); polyvinyl alcohol (PVA); and combinations thereof.

A suitable technique includes forming a solution or slurry containing the constituent components of the film, casting and drying the solution or slurry to form a film. Once dried the film may be cut into segments. Alternatively, the film can be continuously cast and accumulated in roll form. An optional technique for incorporating substances or components into the film can involve producing a film by any suitable technique, and incorporating a component or substance into the film via a surface application technique. For example, the film may be in a state wherein it is not completely dried or cured, the component or substance is then introduced onto the surface thereof, and the drying or curing process completed. The resulting film comprises the component on or near the surface of the film. Modifications of this technique are also possible. For example, a fully dried or cured film may form the starting material. The dried or cured film may then be subjected to a process such as heating or wetting, such that the surface is modified to more readily accept the component or substance. The component or substance can then be added to the modified surface and the film dried or cooled to render a film comprising the component or substance incorporated therein at the surface of the film. Alternatively, a substance or additional component may simply be applied to the surface of a fully dried or cured film.

The magnetically-responsive particles may be introduced into the film in any suitable manner. For instance, the particles can be introduced into the solution or slurry that forms the film so that upon casting and drying the film includes magnetically-responsive particles dispersed within, and trapped by, a dissolvable matrix. Alternatively, the particles may be incorporated into the film via any convenient surface application techniques. Upon dissolution of the film, the magnetic particles are released, and can be, for example, dispersed into a substance or mixture acting as a solvent. The magnetically-responsive particles can be coated or uncoated, treated or untreated, and/or lack any convenient type of surface modification.

Magnetic Separation and Removal of Residual Liquid

In some embodiments the subject methods include a step of magnetically separating ferric oxide (FOX) particles from the solution they are in. As such a magnetic field (e.g., using a magnet) is applied to the sample such that the FOX particles physically cluster with one another. The liquid of the sample present at this point is referred to herein as "residual liquid." In some cases, prior to proceeding to the next step, the residual liquid is removed. In some such cases, 90% or more of the residual liquid (e.g., 95% or more, 98% or more, or 100% of the residual liquid) is removed. In some cases, as much as possible of the residual liquid is removed.

Wash Buffer

In some embodiments, a subject method includes a wash step (e.g., using an acidic wash buffer—see the acidic binding buffer section above for a description of suitable buffers and suitable pH ranges). When included, any number of convenient washes can be performed (e.g., 1×, 2×, 3×, 4×, etc.). In some cases, the wash buffer includes a detergent. In some cases the wash buffer includes an antimicrobial agent (e.g., Proclin 300). In some cases the wash buffer includes a detergent (e.g., Tween-20).

In some cases when wash buffer is used, the sample is mixed (particles mixed with the wash buffer) prior to removing the wash solution. In some such cases the sample is pipetted 3 or more times with wash buffer (e.g., 4 or more, 5 or more, 6 or more, 7 or more, 8 or more, 9 or more, or 10 or more times). In some cases the sample is pipetted about 3 times with wash buffer. In some cases the sample is pipetted about 5 times with wash buffer. In some cases the sample is pipetted about 10 times with wash buffer.

Elution Buffer

The elution buffer may be alkaline in order to elute the nucleic acids from the ferric oxide particles. In some cases, the elution buffer will have a pH in a range of from 10 to 13 (e.g., from 10 to 12.8, 10 to 12.5, 10 to 12, 10.5 to 13, 10.5 to 12.8, 10.5 to 12.5, 10.5 to 12, 11 to 13, 11 to 12.8, 11 to 12.5, 11 to 12, or from 11.3 to 11.8; or a pH of about 11.5, 11.8, 12, or 12.2). In some cases the elution buffer has a pH of from 11.4 to 11.8. In some cases, the elution buffer has a pH in a range of from 11.5 to 12.5. In some cases, the elution buffer has a pH of about 12.

The elution buffer can include any convenient organic and/or inorganic buffering agent. For example, in some cases the elution buffer includes 2-amino-2-hydroxymethyl-1,3-propanediol (Tris, tris(hydroxymethyl)aminomethane). In some case the elution buffer includes potassium hydroxide (e.g., in some cases 50 mM-70 mM, or about 60 mM Potassium Hydroxide).

In some cases, the elution buffer includes Tris and has a pH in a range of from 10 to 13 (e.g., from 10 to 12.8, 10 to 12.5, 10 to 12, 10.5 to 13, 10.5 to 12.8, 10.5 to 12.5, 10.5 to 12, 11 to 13, 11 to 12.8, 11 to 12.5, 11 to 12, or from 11.3 to 11.8; or a pH of about 11.5, 11.8, 12, or 12.2). The elution buffer will in some cases include a buffering agent (e.g., Tris) at a concentration between 1 and 100 mM (e.g., between 1 and 20 mM or between 5 and 15 mM, or about 1, 2, 5, 10, 15, 20, 25, 30, 40, or 50 mM). In some cases, the elution buffer includes a buffering agent (e.g., Tris) at concentration in a range of from 9-11 mM. In some cases, the elution buffer includes a buffering agent (e.g., Tris) at concentration of about 10 mM.

In some embodiments, the elution buffer can include one or more of the following (e.g., in some cases in addition to Tris): (1) 4-(cyclohexylamino)-1-butanesulfonic acid (CABS), (2) 3-(cyclohexylamino)-1-propanesulfonic acid (CAPS), (3) 3-(cyclohexylamino-2-hydroxy-1-propanesulfonic acid (CAPSO), (4) 2-(cyclohexylamino) ethanesulfonic acid (CHES), (5) N-(2-hydroxyethyl)piperazine-N'-(3-propanesulfonic acid) (EPPS), (6) N-(2-hydroxyethyl) piperazine-N'-(2-ethanesulfonic acid (HEPES), (7) 2-(N-morpholino) ethanesulfonic acid (MES), (8) 3-(N-morpholino) propanesulfonic acid (MOPS), (9) piperazine-N,N'-bis(2-ethanesulfonic acid (PIPES), (10) [(2-hydroxy-1,1-bis[hydroxymethyl]ethyl)amino]-1-propanesulfonic acid (TAPS), (11) ethanolamine, and (12) 3-amino-1-propanesulfonic acid. Inorganic buffering agents such as sodium phosphate and potassium phosphate can also be used in some cases, and the elution buffer can include combinations of more than one buffering agent.

In some embodiments, the elution buffer does not include a chelating agent. However, it may be desirable to use a chelating agent. When present, chelating agents can include, but are not limited to EDTA and EGTA (e.g., at a concentration in a range of 0.1 mM to 100 mM, e.g., 0.5 to 50 mM or 1 to 10 mM).

Preservatives, e.g., sodium azide, can in some cases be used (e.g., in a concentration range of about 0.1% to 0.4%). Stabilizers, e.g., polyethylene glycol, can in some cases be used (e.g., in a concentration range of about 0.04% to 1%).

Any convenient elution volume can be used, and the elution volume will likely depend on the amount of starting material. For example, when 200 µL of biological sample is used, the amount of elution buffer used in the elution step can in some cases be in a range of from 10 to 200 µL (e.g., from 10 to 150, 10 to 120, 10 to 100, 10 to 80, 10 to 60, 10 to 50, 10 to 40, 10 to 30, 20 to 200, 20 to 150, 20 to 120, 20 to 100, 20 to 80, 20 to 60, 20 to 50, 20 to 40, 20 to 30, 30 to 200, 30 to 150, 30 to 120, 30 to 100, 30 to 80, 30 to 60, 30 to 50, 30 to 40, 40 to 200, 40 to 150, 40 to 120, 40 to 100, 40 to 80, 40 to 60, 40 to 50, 50 to 200, 50 to 150, 50 to 120, 50 to 100, 50 to 80, or 50 to 60 µL). As another example, in some such cases the amount of elution buffer used in the elution step is about 10, 20, 30, 40, 50, 60, 80, or 100 µL. In some cases the amount of elution buffer used in the elution step is about 30 µL. In some cases the amount of elution buffer used in the elution step is about 40 µL. In some cases the amount of elution buffer used in the elution step is about 50 µL. In some cases the amount of elution buffer used in the elution step is about 100 µL.

The volume of choice can depend on the downstream application of choice. For example, for some downstream applications increased overall yield may be more important than concentration, and one may choose to use a higher elution volume to increase overall yield; while for other downstream applications increased concentration may be more important than overall yield, and one may choose to use a reduced elution volume to increase concentration.

The volumes presented as specific values (e.g., "x" µL) throughout the figures and text of the disclosure (for all reagents used in the subject methods—not just those discussed in relation to the elution buffer), can be scaled based on the starting volume of the biological sample. As an illustrative example, in some cases the amount of elution buffer used in the elution step is in a range of from 0.05 to 1 volumes (relative to the starting volume of the biological sample) (e.g., from 0.05 to 0.8, 0.05 to 0.6, 0.05 to 0.5, 0.05 to 0.4, 0.05 to 0.3, 0.05 to 0.2, 0.05 to 0.1, 0.1 to 1, 0.1 to 0.8, 0.1 to 0.6, 0.1 to 0.5, 0.1 to 0.4, 0.1 to 0.3, 0.1 to 0.2, 0.1 to 0.1, 0.15 to 1, 0.15 to 0.8, 0.15 to 0.6, 0.15 to 0.5, 0.15 to 0.4, 0.15 to 0.3, 0.15 to 0.2, 0.15 to 0.1, 0.2 to 1, 0.2 to 0.8, 0.2 to 0.6, 0.2 to 0.5, 0.2 to 0.4, 0.2 to 0.3, 0.2 to 0.2, 0.2 to 0.1, 0.25 to 1, 0.25 to 0.8, 0.25 to 0.6, 0.25 to 0.5, 0.25 to 0.4, 0.25 to 0.3, 0.25 to 0.2, or 0.25 to 0.1 volumes). In some cases the amount of elution buffer used in the elution step is about 0.05, 0.1, 0.15, 0.2, 0.25, 0.3, 0.4, or 0.5 volumes (relative to the starting volume of the biological sample). In some cases the amount of elution buffer used in the elution step is about 0.15 volumes (relative to the starting volume of the biological sample). In some cases the amount of elution buffer used in the elution step is about 0.2 volumes (relative to the starting volume of the biological sample). In some cases the amount of elution buffer used in the elution step is about 0.225 volumes (relative to the starting volume of the biological sample). In some cases the amount of elution buffer used in the elution step is about 0.5 volumes (relative to the starting volume of the biological sample).

In some embodiments, thorough mixing of the FOX particles with the elution buffer can be accomplished by pipetting. In some such cases the sample is pipetted 3 or more times after adding elution buffer (e.g., 4 or more, 5 or more, 8 or more, 10 or more, 12 or more, 15 or more, or 18 or more times). In some cases the sample is pipetted 15 or more times after adding elution buffer. In some cases the sample is pipetted about 20 times after adding elution buffer.

Neutralization Reagent

In some cases (e.g., to facilitate downstream applications), e.g., because the elution buffer is alkaline, it is desirable to neutralize the pH of the eluted nucleic acid sample. Because nucleic acids tend to be stable at slightly alkaline pH (e.g., pH higher than 7), the term "neutralization" is not meant to imply that the final pH of the solution will be 7. The term "neutralize" as used herein does not necessarily mean that the final pH of the solution is 7, but instead means bringing the pH of a solution closer to 7 than it was previously. For example, if the eluted alkaline nucleic acid sample is at a pH in a range of from 10 to 12—a step of neutralizing the solution can result in binging the pH of the solution to a range of from 7.2 to 9 (e.g., about 7.2, about 7.5, about 7.6, about 8, about 8.2, and the like) (e.g., by adding neutralization buffer). As such, in some cases, a subject method includes a step of adding a neutralization agent (e.g., a neutralization buffer, an acid) to an eluted nucleic acid sample in order to lower the pH of the sample.

Conjugated Particles—Depletion—Identification

Aspects of the disclosure include ferric oxide (FOX) particles that are conjugated to a nucleic acid probe (e.g., DNA probe) that is complementary to a target microRNA (e.g., an abundant miRNA). In some cases a population of conjugated FOX particles (conjugated to a nucleic acid probe that is complementary to a target microRNA) can be provided as part of a dissolvable film (e.g., see discussion of dissolvable film elsewhere in this disclosure).

In some embodiments a subject method includes depleting a sample of one or more abundant miRNAs, e.g., so that the abundant miRNAs do not interfere with analyses focused on less abundant miRNAs. In such a case, the conjugated FOX particles mentioned above can be used to contact the sample such that the target miRNA (e.g., an abundant miRNA) binds to the conjugated FOX particles, and the particles are then separated from the sample, thus depleting the sample of the targeted miRNA. In some such cases the targeted abundant miRNA is one or more miRNAs selected from: miR-191, miR-320, miR-29b, miR-143, miR-145, and miR-424. As another example, in some cases it might be desirable to identify a biomolecule (e.g., an mRNA) that is bound to a given target miRNA. As such, a the conjugated FOX particles mentioned above can be used to contact a sample such that the target miRNA of interest binds to the conjugated FOX particles—and the targeted miRNA also remains bound the biomolecule it was bound to prior to contact with the FOX particles. Thus, once the conjugated FOX particles are separated from the sample, they can be analyzed to identify biomolecules that 'co-purified' with the targeted miRNA. Thus, conjugated FOX particles of the disclosure can be used to identify biomolecules (e.g., RNAs) that bind to a given target miRNA.

In some embodiments in which conjugated FOX particles (FOX particles conjugated to a nucleic acid probe that is complementary to a target microRNA) are used, 20% or more of the ferric oxide particles of the population (e.g., 40% or more, 50% or more, 70% or more, 85% or more, 90% or more, or 100% of the ferric oxide particles of the population) are conjugated to a nucleic acid probe that is complementary to the same microRNA (e.g., same abundant miRNA). In some cases in which conjugated FOX particles (FOX particles conjugated to a nucleic acid probe that is complementary to a target microRNA) are used, 20% or more of the ferric oxide particles of the population (e.g., 40% or more, 50% or more, 70% or more, 85% or more, 90% or more, or 100% of the ferric oxide particles of the population) are conjugated to the same nucleic acid probe (e.g., the same DNA probe). A given population of conjugated FOX particles (FOX particles conjugated to a nucleic acid probe that is complementary to a target microRNA) can include particles that are each conjugate to probes that target different miRNAs. For example, in some cases a population of conjugated FOX particles includes a first particle that is conjugated to a first nucleic acid probe (e.g., DNA probe), and includes a second particle that is conjugated to a second nucleic acid probe (e.g., DNA probe), where the first and second nucleic acid probes are complementary to different targeted microRNAs (e.g., different abundant miRNAs).

Downstream Uses miRNA from cells or circulating in the blood can be used as diagnostic indicators or surrogate markers for therapy. As such, the nucleic acids (e.g., miRNAs) extracted using the methods and compositions of the disclosure can be used for any convenient application, including diagnostic and prognostic methods. For example, extracted miRNAs can be used as diagnostic and/or prognostic biomarkers in methods performed to diagnose/prognose a condition (e.g., diagnose a disease or condition such as cancer, cardiovascular disease, neuromuscular disease, diabetes, breast cancer, infectious disease, and the like; predict wither a given individual will be responsive to a given drug, e.g., a drug used to treat a disease like cancer; etc.). As an example, the subject methods can be used to diagnose a patient suspected of having cancer or of having a pre-cancerous condition. Liquid biopsies, in conjunction with predictive and prognostic biomarkers, have the potential to play an important role in precision or personalized medicine. This disclosure provides robust methods for extracting and isolate miRNA from a variety of biological specimens.

Thus in some cases a subject method includes measuring the abundance of one or more nucleic acids (e.g., miRNAs) present in the extracted nucleic acid sample.

Any convenient measuring technique can be used. For example, in some cases the measuring includes one or more of: nucleic acid sequencing, e.g., via next generation sequencing (NGS) protocols, quantitative RT-PCR, strand displacement amplification (SDA), and microarray hybridization. In some cases, once a target nucleic acid (e.g., miRNA) or target population of nucleic acids (e.g., multiple miRNAs) is measured, the values can be used for a number of different purposes, including for diagnoses/prognoses.

Kits

Also provided are reagents, compositions and kits thereof for practicing one or more of the above-described methods. The subject reagents, compositions and kits thereof may vary greatly and can include any combination of one or more of: (i) ferric oxide (FOX) particles (e.g., as part of a dissolvable film); (ii) a protease (e.g., proteinase K); (iii) an acidic buffer for binding nucleic acids to the ferric oxide particles; (iv) an alkaline elution buffer for releasing nucleic acids from the ferric oxide particles; (v) a control microRNA (e.g., for a positive control); (vi) a cellular lysis buffer; (vii) DNase; (viii) a magnet; (ix) an acidic wash solution; and (x) ferric oxide particles that are conjugated to a nucleic acid probe that is complementary to a target microRNA (e.g., miR-191, miR-320, miR-29b, miR-143, miR-145, miR-424, and the like). The various components of the may be present in separate containers, or some or all of them may be pre-combined into a single reagent mixture or single container.

In addition to the above components, the subject kits may further include (in certain embodiments) instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, and the like. Yet another form of these instructions is a computer readable medium, e.g., diskette, compact disk (CD), flash drive, and the like, on which the information has been recorded. Yet another form of these instructions that may be present is a website address which may be used via the internet to access the information at a removed site.

Exemplary Non-Limiting Aspects of the Disclosure

Aspects, including embodiments, of the present subject matter described above may be beneficial alone or in combination, with one or more other aspects or embodiments. Without limiting the foregoing description, certain non-limiting aspects of the disclosure are provided below and numbered 1-62. As will be apparent to those of ordinary skill in the art upon reading this disclosure, each of the individually numbered aspects may be used or combined with any of the preceding or following individually numbered aspects. This is intended to provide support for all such combinations of aspects and is not limited to combinations of aspects explicitly provided below:

1. A method of extracting nucleic acids from a biological sample, the method comprising:
   (a) contacting a biological sample comprising nucleic acids with proteinase K at a temperature in a range of from 47° C. to 53° C. for a period of time in a range of from 10 to 40 minutes, to degrade proteins present in the sample, thereby producing a proteinase K treated sample; (b) contacting the proteinase K treated sample with ferric oxide particles under acidic conditions to induce binding between the ferric oxide particles and the nucleic acids; (c) magnetically separating the nucleic acid bound ferric oxide particles from the proteinase K treated sample; (d) contacting the nucleic acid bound ferric oxide particles with an alkaline elution buffer to release the nucleic acids from the ferric oxide particles into the alkaline elution buffer, thereby generating an alkaline nucleic acid sample; and (e) magnetically separating the ferric oxide particles from the alkaline nucleic acid sample, thereby generating a sample of extracted nucleic acids.

2. The method of 1, further comprising, after the magnetic separating of step (e), neutralizing the alkaline nucleic acid sample by contacting it with a buffered solution to generate the sample of extracted nucleic acids.

3. The method 1 or 2, wherein the proteinase K treated sample is contacted in step (b) with a dissolvable film comprising the ferric oxide particles, whereby the film dissolves and releases the ferric oxide particles.

4. The method of 3, wherein the film is formed from a material comprising at least one of: hydroxyalkylmethyl cellulose; carboxymethyl cellulose; carboxylic hydroxyalkyl ester monomer; ethoxylated hydroxyalkyl(meth)acrylate; propoxylated hydroxyalkyl(meth)acrylate; polyethylene glycol (PEG); polyvinyl alcohol (PVA); and combinations thereof.

5. The method of any one of 1-4, wherein step (b) comprises mixing the proteinase K treated sample with the ferric oxide particles by pipetting 5 or more times.

6. The method of any one of 1-5, wherein step (c) comprises removal of 90% or more of the proteinase K treated sample.

7. The method of any one of 1-6, wherein the sample of extracted nucleic acids comprises microRNAs.

8. The method of 7, further comprising a step of identifying a biomolecule that is bound to one or more of the microRNAs.

9. The method of any one of 1-8, wherein the method does not include use of chloroform or phenol.

10. The method of any one of 1-9, wherein the method is completed in less than 30 minutes.

11. The method of any one of 1-10, wherein the biological sample comprises nucleic acids that are cross-linked.

12. The method of any one of 1-11, wherein the biological sample is a whole blood sample.

13. The method of any one of 1-12, wherein the biological sample comprises cells.

14. The method of 13, wherein the method comprises lysing cells of the biological sample prior to step (a).

15. The method of 14, wherein the lysing comprises contacting the biological sample with an alkaline diluent.

16. The method of any one of 1-15, wherein the biological sample comprises fixed cells.

17. The method of any one of 1-16, wherein the biological sample is a formalin-fixed paraffin-embedded (FFPE) tissue sample 18. The method of any one of 1-17, wherein the biological sample is a biopsy.

19. The method of any one of 1-11, wherein the biological sample is a serum sample.

20. The method of any one of 1-11, wherein the biological sample is a plasma sample.

21. The method of any one of 1-20, wherein the biological sample is from an individual suspected of having cancer or of having a pre-cancerous condition.

22. The method of any one of 1-21, wherein the method further comprises depleting an abundant microRNA from the proteinase K treated sample prior to step (b) and/or after step (e).

23. The method of 22, wherein the abundant microRNA is selected from the group consisting of: miR-191, miR-320, miR-29b, miR-143, miR-145, and miR-424.

24. The method of 22 or 23, wherein the depleting comprises (i) contacting the proteinase K treated sample with ferric oxide particles that are conjugated to a nucleic acid probe that hybridizes with the abundant microRNA, and (ii) separating the probe-conjugated ferric oxide particles, hybridized with the abundant microRNA, from the proteinase K treated sample.

25. The method of any one of 1-24, comprising measuring the abundance of one or more nucleic acids present in the sample of extracted nucleic acids.

26. The method of 25, wherein said measuring comprises one or more of: nucleic acid sequencing, quantitative RT-PCR, strand displacement amplification (SDA), and hybridization to a microarray.

27. The method of any one of 1-26, further comprising making a diagnosis of an individual based on the measuring.

28. A population of ferric oxide particles, comprising ferric oxide particles that are conjugated to a nucleic acid probe that is complementary to an abundant microRNA.

29. The population of ferric oxide particles of 28, wherein the abundant microRNA is selected from the group consisting of: miR-191, miR-320, miR-29b, miR-143, miR-145, and miR-424.

30. The population of ferric oxide particles of 28 or 29, wherein 20% or more of the ferric oxide particles of the population are conjugated to a nucleic acid probe that is complementary to the same abundant microRNA.

31. The population of ferric oxide particles of any one of 28-30, wherein 50% or more of the ferric oxide particles of the population are conjugated to a nucleic acid probe that is complementary to the same abundant microRNA.
32. The population of ferric oxide particles of any one of 28-31, wherein 20% or more of the ferric oxide particles of the population are conjugated to the same nucleic acid probe.
33. The population of ferric oxide particles of any one of 28-32, wherein 50% or more of the ferric oxide particles of the population are conjugated to the same nucleic acid probe.
34. The population of ferric oxide particles of any one of 28-33, wherein a first particle of the population is conjugated to a first nucleic acid probe and a second particle of the population is conjugated to a second nucleic acid probe, wherein the first and second nucleic acid probes are complementary to different abundant microRNAs.
35. A dissolvable film comprising the population of ferric oxide particles of any one of 28-34.
36. The dissolvable film of 35, wherein the film is formed from a material comprising at least one of: hydroxyalkylmethyl cellulose; carboxymethyl cellulose; carboxylic hydroxyalkyl ester monomer; ethoxylated hydroxyalkyl (meth)acrylate; propoxylated hydroxyalkyl(meth)acrylate; polyethylene glycol (PEG); polyvinyl alcohol (PVA); and combinations thereof.
37. A kit, comprising: ferric oxide particles; proteinase K; an acidic buffer for binding nucleic acids to the ferric oxide particles; an alkaline elution buffer for releasing nucleic acids from the ferric oxide particles; and a control microRNA.
38. The kit of 37, wherein the kit comprises two or more control microRNAs.
39. The kit of 37 or 38, further comprising a cellular lysis buffer or DNase.
40. The kit of any one of 37-39, further comprising a magnet.
41. The kit of any one of 37-40, further comprising an acidic wash solution.
42. The kit of any one of 37-41, wherein the proteinase K is lyophilized.
43. The kit of 42, further comprising a diluent for the proteinase K.
44. The kit of any one of 37-43, wherein the kit comprises a dissolvable film comprising the ferric oxide particles.
45. The kit of 44, wherein the dissolvable film is formed from a material comprising at least one of: hydroxyalkylmethyl cellulose; carboxymethyl cellulose; carboxylic hydroxyalkyl ester monomer; ethoxylated hydroxyalkyl (meth)acrylate; propoxylated hydroxyalkyl(meth)acrylate; polyethylene glycol (PEG); polyvinyl alcohol (PVA); and combinations thereof.
46. The kit of any one of 37-45, further comprising ferric oxide particles that are conjugated to a nucleic acid probe that is complementary to an abundant microRNA.
47. The kit of 46, wherein the abundant microRNA is selected from the group consisting of: miR-191, miR-320, miR-29b, miR-143, miR-145, and miR-424.
48. The kit of 46 or 47, wherein 20% or more of the DNA-conjugated ferric oxide particles are conjugated to a nucleic acid probe that is complementary to the same abundant microRNA.
49. The kit of any one of 46-48, wherein 50% or more of the DNA-conjugated ferric oxide particles are conjugated to a nucleic acid probe that is complementary to the same abundant microRNA.
50. The kit of any one of 46-49, wherein 20% or more of the DNA-conjugated ferric oxide particles are conjugated to the same nucleic acid probe.
51. The kit of any one of 46-50, wherein 50% or more of the DNA-conjugated ferric oxide particles are conjugated to the same nucleic acid probe.
52. The kit of any one of 46-51, wherein a first DNA-conjugated ferric oxide particle is conjugated to a first nucleic acid probe and a second DNA-conjugated ferric oxide particle is conjugated to a second nucleic acid probe, wherein the first and second nucleic acid probes are complementary to different abundant microRNAs.
53. The kit of any one of 46-52, comprising a dissolvable film that comprises the DNA-conjugated ferric oxide particles.
54. The kit of 53, wherein the film is formed from a material comprising at least one of: hydroxyalkylmethyl cellulose; carboxymethyl cellulose; carboxylic hydroxyalkyl ester monomer; ethoxylated hydroxyalkyl(meth)acrylate; propoxylated hydroxyalkyl(meth)acrylate; polyethylene glycol (PEG); polyvinyl alcohol (PVA); and combinations thereof.
55. A method for identifying biomolecules that bind to microRNAs, the method comprising: contacting a biological sample comprising microRNAs and their target biomolecules, with a population of ferric oxide particles, wherein the population of ferric oxide particles comprises ferric oxide particles conjugated to a nucleic acid probe that is complementary to a target microRNA; magnetically separating the ferric oxide particles from the biological sample to generate a sample comprising the ferric oxide particles bound to the target miRNA, wherein the target miRNA is bound to a biomolecule from the biological sample; and identifying the biomolecule to which the target miRNA is bound.
56. The method according to 55, wherein 20% or more of the ferric oxide particles of the population are conjugated to a nucleic acid probe that is complementary to the same microRNA.
57. The method according to 55, wherein 50% or more of the ferric oxide particles of the population are conjugated to a nucleic acid probe that is complementary to the same microRNA.
58. The method according to any of 55-57, wherein 20% or more of the ferric oxide particles of the population are conjugated to the same nucleic acid probe.
59. The method according to any of 55-57, wherein 50% or more of the ferric oxide particles of the population are conjugated to the same nucleic acid probe.
60. The method according to any of 55-59, wherein a first particle of the population is conjugated to a first nucleic acid probe and a second particle of the population is conjugated to a second nucleic acid probe, wherein the first and second nucleic acid probes are complementary to different microRNAs.
61. The method according to any of 55-60, wherein the biological sample is contacted with a dissolvable film comprising the ferric oxide particles, whereby the film dissolves and releases the ferric oxide particles.
62. The method of 61, wherein the film is formed from a material comprising at least one of: hydroxyalkylmethyl cellulose; carboxymethyl cellulose; carboxylic hydroxyalkyl ester monomer; ethoxylated hydroxyalkyl(meth)acrylate; propoxylated hydroxyalkyl(meth)acrylate; polyethylene glycol (PEG); polyvinyl alcohol (PVA); and combinations thereof.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric. In addition, common laboratory protocol abbreviations may be used (e.g., hr=hours, min=minutes, ml=milliliters, ul=microliters, rpm=revolutions per minute, g (in the context of centrifugation)=times the force of gravity, etc.).

The following experiments led to improved FOX extraction protocols that reliably extract amplifiable nucleic acids (e.g., miRNAs) from a variety of sample types including whole blood, blood plasma, blood serum, FFPE, and cancer cells. In some cases, the total extraction time was reduced by 30 minutes, while at the same time increasing sensitivity. The improved protocols can be used to extract DNA in addition to miRNA. The improved protocols do not require centrifugation or spin-column steps for size selection, reducing the overall cost of consumables for the nucleic acid isolation. Unlike miRNA isolation kits currently in the marketplace (e.g., miRVANA), the protocols described herein do not require harsh chemicals such as chloroform and phenol (which require added safety precautions and can negatively affect downstream applications such as PCR). Additionally, the cost per reaction for the improved protocols described herein, compared to that of other kits, is 10× less expensive (based on catalog prices advertised as research reagents).

Thus, the data presented in the following examples demonstrate that the methods and compositions of the disclosure can be used to efficiently extract nucleic acids (e.g., miRNAs) from a variety of biological sample types. The data show that specific miRNAs can be detected within the extracted nucleic acids, and the detected expression levels of example miRNAs were statistically identical to those detected using the gold standard miRNA isolation system on the market. The methods of the disclosure were more cost-effective and safer than alternative methods. Moreover, after testing various biological samples, there is yet to be a sample that is incompatible with the subject methods. Thus the nucleic acid (e.g., miRNA) isolation system provided here can be used on any sample (formalin-fixed paraffin-embedded (FFPE), blood, serum, plasma, cells, etc.) and can be considered best in its class.

Three observations from the experiments presented below include: (i) PCR replicates (for detection of specific target miRNAs from the extracted nucleic acids) were excellent and the variability in the Ct values of the spike-in templates were satisfactory; (ii) the FOX-based miRNA extractions provided comparable results to the gold standard method in terms of Ct values; and (iii) the improved protocols improved the quality and quantity of extracted nucleic acids.

Figure 2:
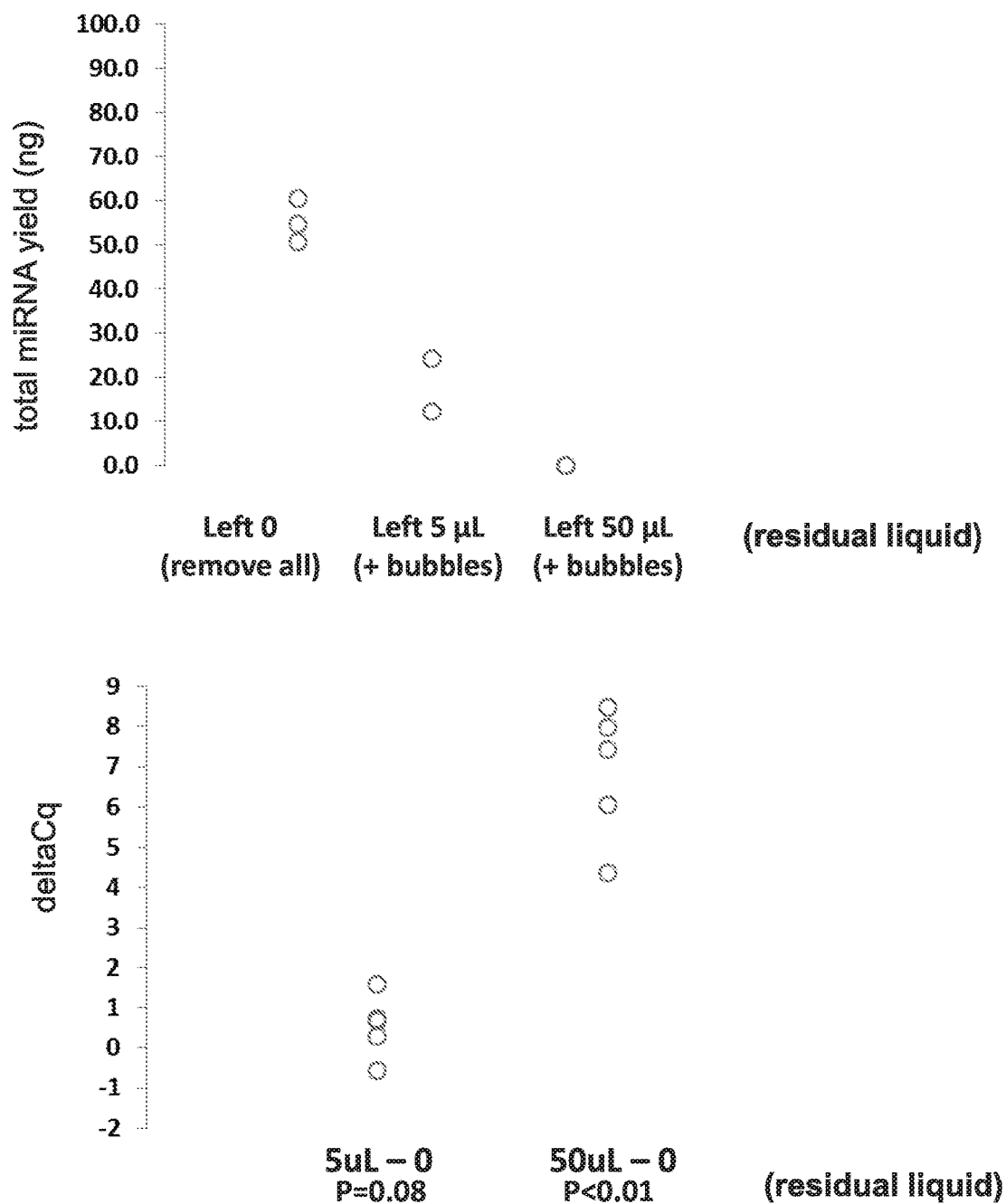
FIG. 2 depicts results obtained from evaluating whether removal of all residual liquid at steps 5 and 7 (after applying a magnetic field), versus leaving some residual liquid behind (e.g., 5 µL or 50 µL of residual) affected yield of miRNA.
Figure 3:
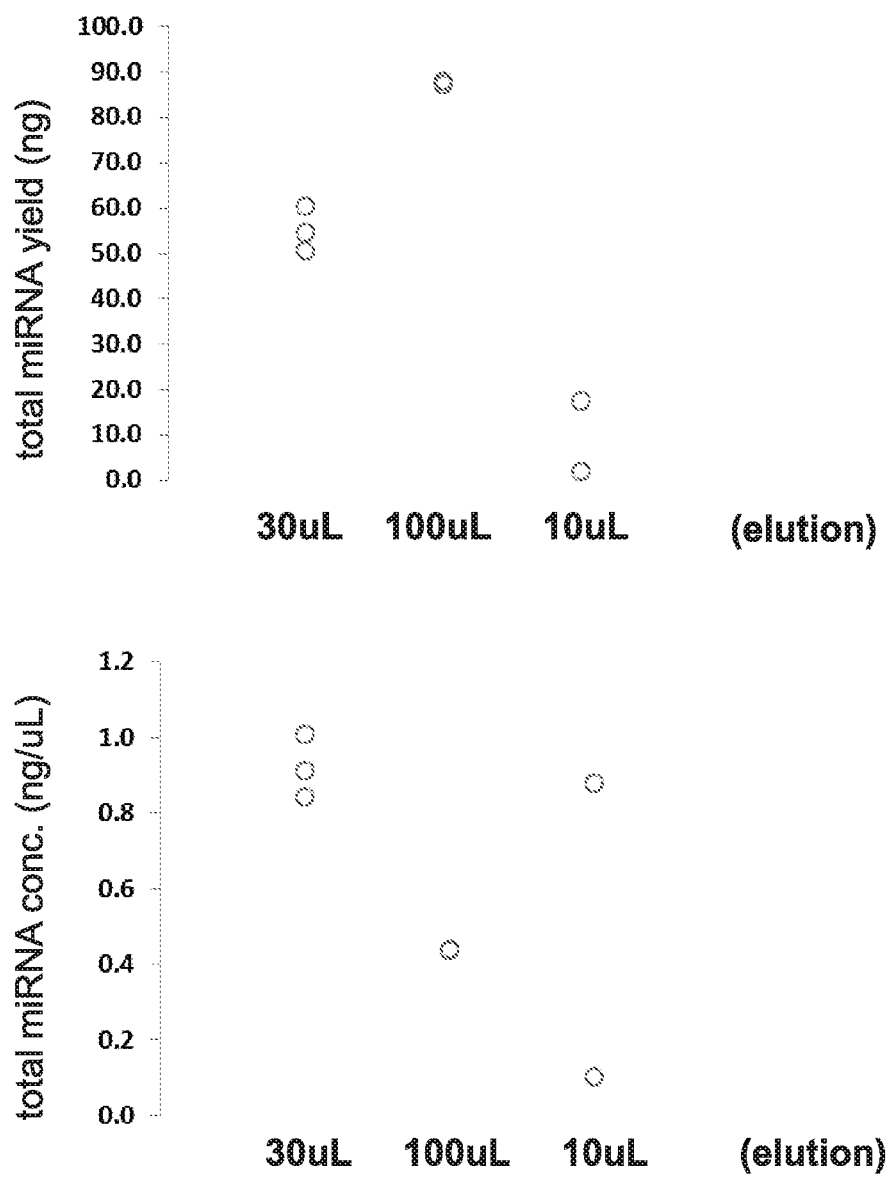
FIG. 3 depicts results obtained from evaluating whether using different elution volumes improved the yield of miRNA.
Figure 4:
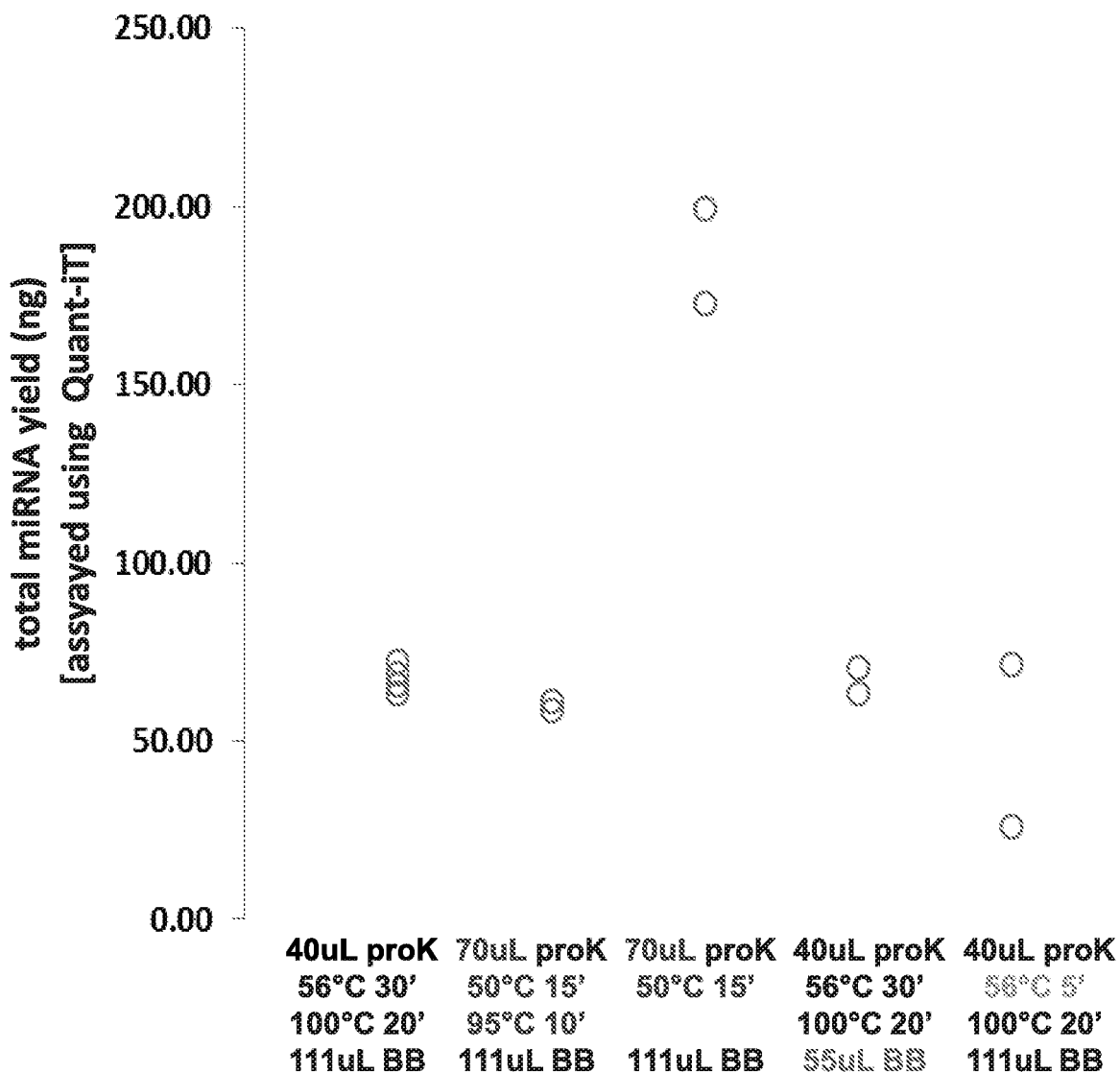
FIG. 4 depicts results from experiments testing whether various modifications to a FOX-based method for nucleic acid extraction (e.g., amount of proteinase K used, temperature of incubation with proteinase K, and volume of binding buffer) would increase yield of miRNA and/or increase the sensitivity of detection when assaying for the presence of specific miRNAs in the extracted nucleic acid sample.

Example 1—Evaluate Parameters: Mixing, Residual Liquid, Elution Volume (FIGS. 1-3)

Starting with the protocol for DNA extraction depicted on the left side of FIG. 19, various steps were altered with the goal of arriving at improved protocols that allow for efficient extraction of miRNA. As shown in Examples 3 (FIG. 9) and 4 (FIG. 16) below, subject methods for efficient extraction of miRNA can also be used for efficient extraction of mRNA and DNA as well.

Starting with the protocol for DNA extraction depicted on the left side of FIG. 19, the following were steps were manipulated: (i) removing all residual liquid at steps 5 and 7 versus leaving some residual liquid behind (e.g., 5 μL or 50 μL of residual); (ii) varying the volumes added at steps 8 and 10 (e.g., 10, 20, 30, 40, 50, 100 μL); (iii) removing steps such as using no HPV LBC Diluent, using no proteinase K, or not incubating at steps 1 and 2. miRNA yield was determined using microRNA Quant-it, and miRNA abundance (copies per ng total RNA) was determined by MiRXES RT-qPCR.

FIG. 1 depicts results obtained from evaluating whether the amount of mixing prior to elution affected yield of miRNA. The results indicated that insufficient pipetting reduced yield and abundance.

Protocol Used for FIG. 1
1. +850 μL Human papillomavirus (HPV) Liquid Based Cytology (LBC) Diluent and 40 μL Proteinase K to 200 μL serum;
2. 56° C. 30 min, 100° C. 20 min, then cool to <40° C.;
3. Transfer all heated sample to FOX extraction tube, pipette X times* for the film to dissolve;
4. +111 μL Binding Buffer, pipette X times to mix;
5. Put on magnet, remove all liquid and bubbles;
6. +950 μL Wash Buffer, pipette X times to mix;
7. Put on magnet, remove all liquid and bubbles;
8. +30 μL Elution Buffer, pipette X times to mix;
9. Put on magnet, transfer 30 μL liquid to a new tube;
10. +30 μL Neutralization Buffer to the new tube.

Notes
(a) X was 1, 2, 3, 4, 6, 8, or 10 (experiments were performed with multivariate design to help determine at what steps mixing could be modified to improve extraction)
(b) "Binding Buffer" was Sodium Phosphate, pH 1.5-2.0 (Sulfuric Acid was used to bring pH of the buffer in range)
(c) "Wash Buffer" was Proclin 300-Tween-20 Solution pH~2.0

FIG. 2 depicts results obtained from evaluating whether removal of all residual liquid at steps 5 and 7 (versus leaving some residual liquid behind, e.g., 5 μL or 50 μL of residual) affected yield of miRNA.

Protocol Used for FIG. 2
1. +850 μL HPV LBC Diluent and 40 μL Proteinase K to 200 μL serum;
2. 56° C. 30 min, 100° C. 20 min, then cool to <40° C.;
3. Transfer all heated sample to FOX extraction tube, pipette 10 times for the film to dissolve;
4. +111 μL Binding Buffer, pipette 10 times to mix;
5. Apply magnet,
    remove (all liquid and bubbles vs leave 5 μl or 50 μl residual)
6. +950 μL Wash Buffer, pipette 10 times to mix;
7. Apply magnet,
    remove (all liquid and bubbles vs leave 5 μl or 50 μl residual)
8. +30 μL Elution Buffer, pipette 10 times to mix;
9. Put on magnet, transfer 30 μL liquid to a new tube;
10. +30 μL Neutralization Buffer to the new tube.

FIG. 3 depicts results obtained from evaluating whether using different elution volumes improved the yield of miRNA. The results indicated that increasing elution volume (e.g., to 100 µL) increased overall yield.

Protocol Used for FIG. 3
1. +850 µL HPV LBC Diluent and 40 µL Proteinase K to 200 µL serum;
2. 56° C. 30 min, 100° C. 20 min, then cool to <40° C.;
3. Transfer all heated sample to FOX extraction tube, pipette 10 times for the film to dissolve;
4. +111 µL Binding Buffer, pipette 10 times to mix;
5. Put on magnet, remove all liquid and bubbles
6. +950 µL Wash Buffer, pipette 10 times to mix;
7. Put on magnet, remove all liquid and bubbles
8. +X µL Elution Buffer*, pipette 10 times to mix;
9. Put on magnet, transfer X µL liquid* to a new tube;
10. +30 µL Neutralization Buffer to the new tube.
Notes
X was 10, 20, 30, 40, 50, or 100

Example 2—Evaluate Parameters: Proteinase K and Others (FIGS. 4-8)

Various modifications (e.g., amount of proteinase K used, temperature of incubation with proteinase K, and volume of binding buffer) were incorporated into the FOX extraction protocol with the objective of testing whether these modifications could increase yield of miRNA. The Invitrogen Quant-iT RNA Assay Kit was used to quantify total miRNA yield (Each circle represents a technical replicate) and qPCR was used to measure the level of miR-16 (raw Ct values are presented). The data are presented in FIG. 4. In additional to miR-16, four other miRNAs (miR-21, miR-99b, miR-181a, and miR-451a) were also tested, and the improvements to the protocol were reproduced.

Figure 5:
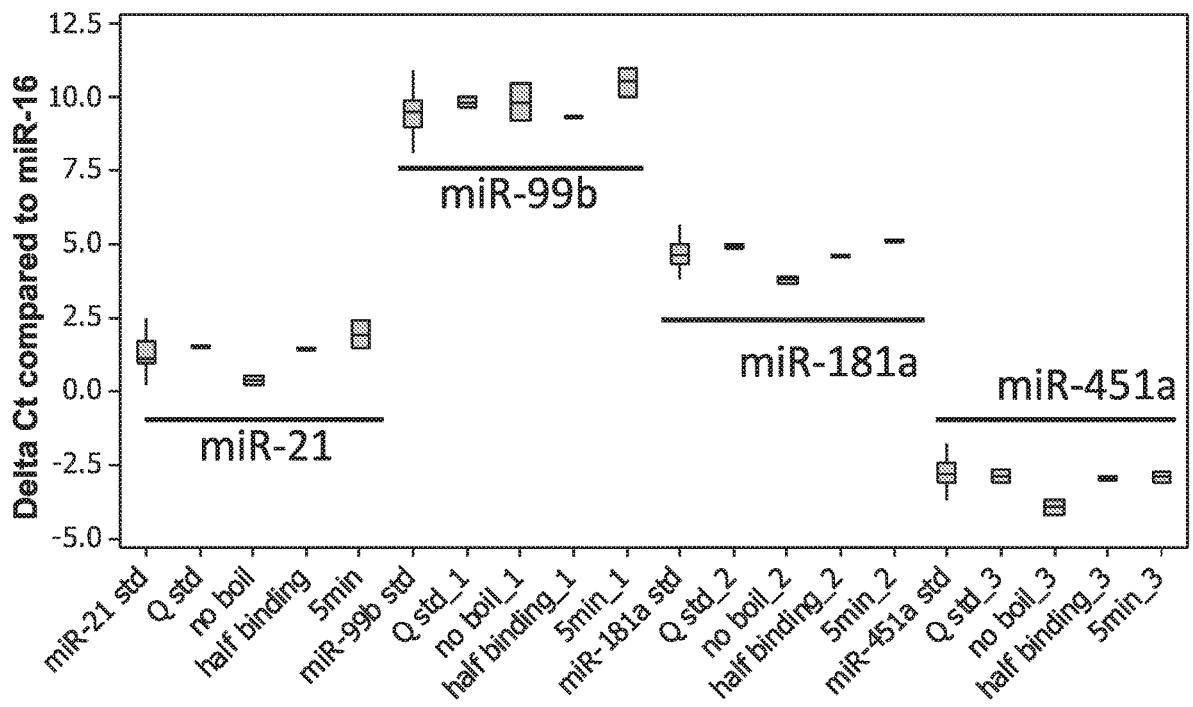
FIG. 5 depicts results from experiments testing whether omitting a denaturation step ("boiling"— to deactivate proteinase K) or reducing the binding buffer/Proteinase K incubation time during the nucleic acid (miRNA) extraction method would improve detection of miRNAs from the extracted nucleic acids.

It was then tested whether omitting a boiling step or reducing the binding buffer/Pro K incubation time at 56° C. from 30 to 5 minutes would improve detection of miRNAs (miR-16 value was considered the gold standard and this was compared to delta Ct values for miR-21, miR-99b, miR-181a, and miR-451a) (FIG. 5). The improved FOX extraction method (see right side of FIG. 19) was compared directly with the Qiagen miRNA Easy protocol ("0 std").

Figure 6:
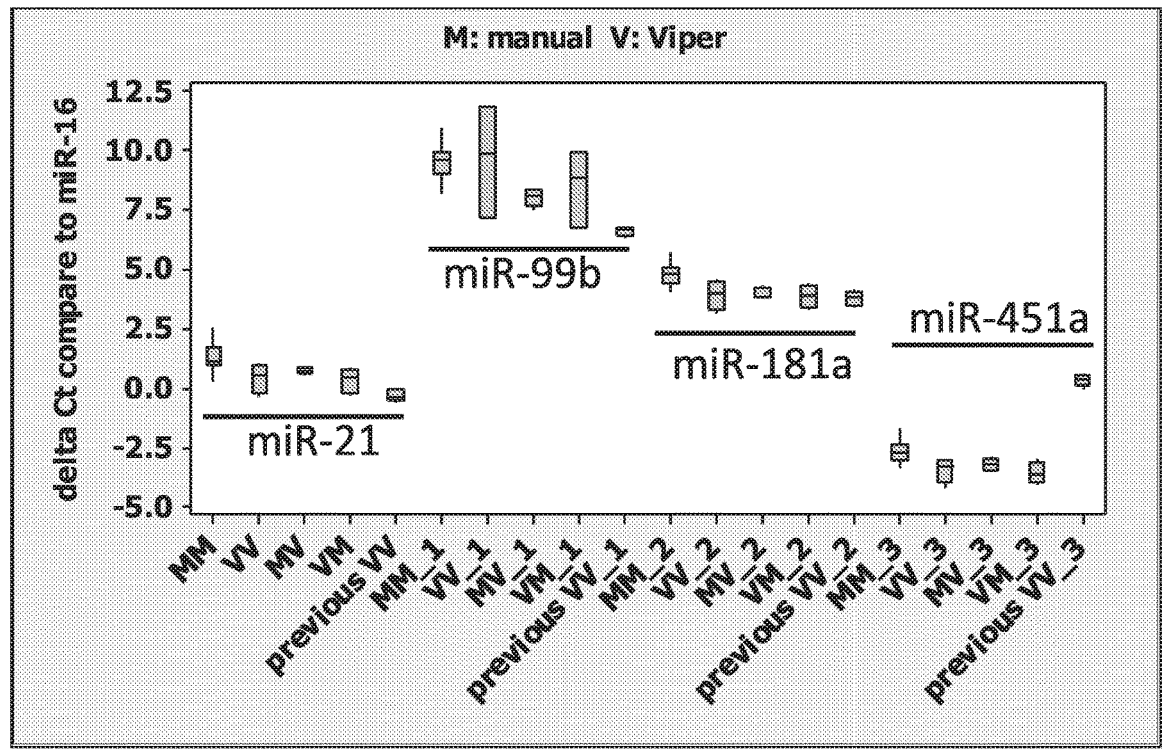
FIG. 6 depicts results from experiments testing whether the improved FOX-based nucleic acid extraction method could be ported onto the BD Viper LT automation platform.

It was then tested whether the new optimized FOX extraction protocol could be ported onto the BD Viper LT automation platform (FIG. 6). Again, the miR-16 delta Ct value was used as the gold standard. MM=manual miRNA extraction/manual miR-16 detection method using qPCR. VV=full Viper LT automation, MV=manual miRNA extraction/Viper LT automated detection, VM=Viper LT automated miRNA extraction/manual detection on lab bench. The delta Ct values correlate well with gold standard but more variability was detected when using full or partial automation.

Figure 7:
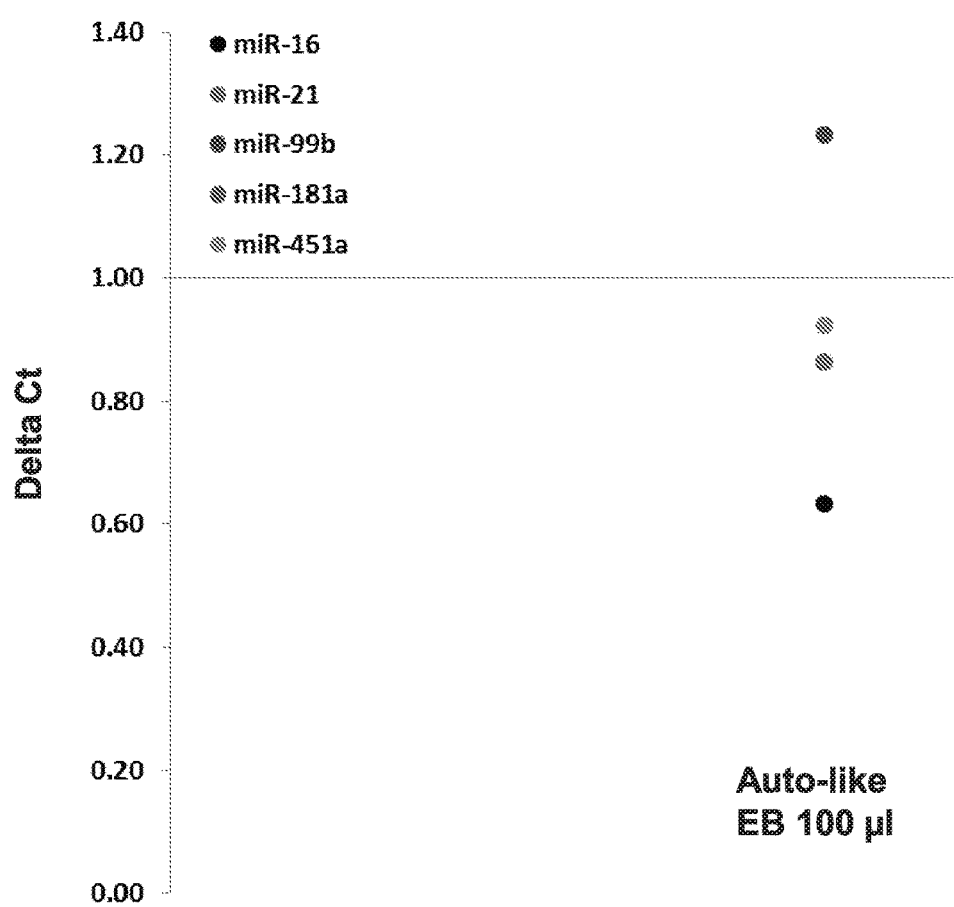
FIG. 7, Panels A-F. (Panel A) Mimicking the volume limitations of the BD Viper LT platform was attempted to evaluate whether elution in 100 ul instead of 50 ul would increase detection of miRNAs. Anything below 1.0 indicates an improvement. (Panel B) Evaluated the improved protocol (right side FIG. 19) ("std") versus adding two FOX wafers ("2 ribbons") versus adding proteinase K prior to addition of the diluent ("proK before HDB") versus adding proteinase K with the addition of only half of the diluent ("0.5 HDB"). (Panel C) Evaluated whether changing the volume of diluent improved detection of miRNAs. (Panel D) Evaluated whether addition of DNase and washing improved detection of miRNAs. (Panel E) Evaluated 2× vs 3× washes and variable amounts of Neutralization Buffer to eluate. (Panel F) Repeated 2× wash experiment and extracting miRNA using 700 uL diluent.
Figure 7:
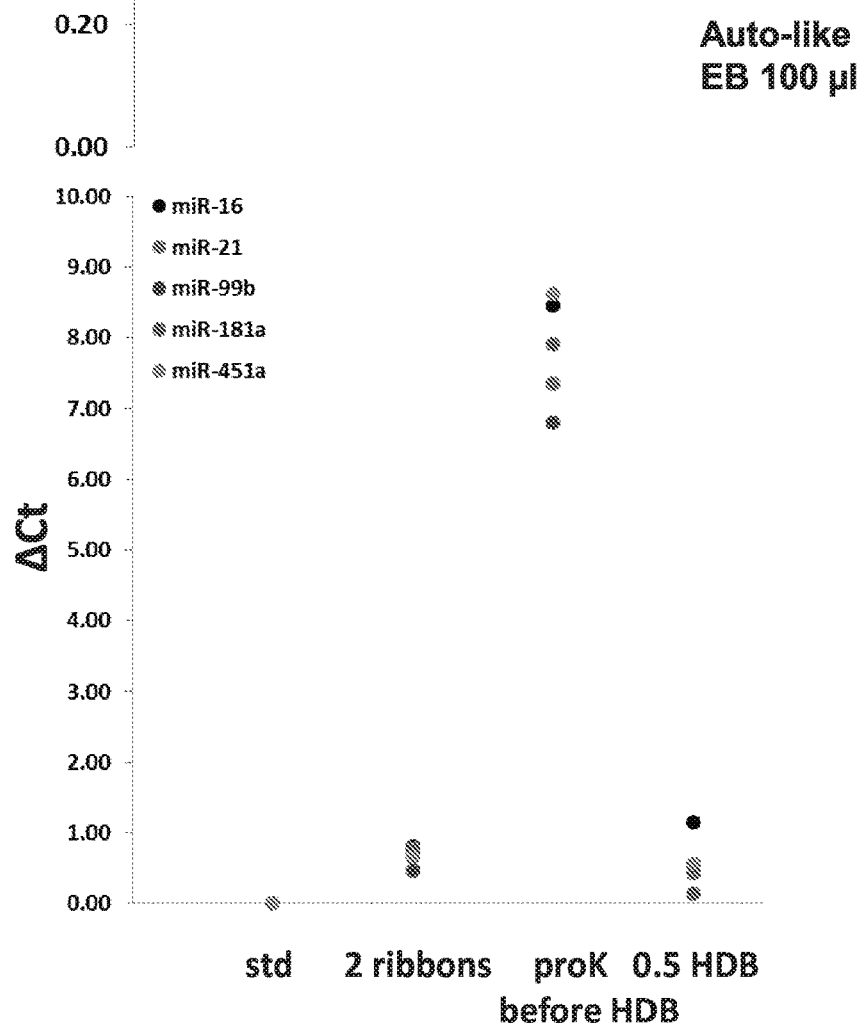
Figure 8:
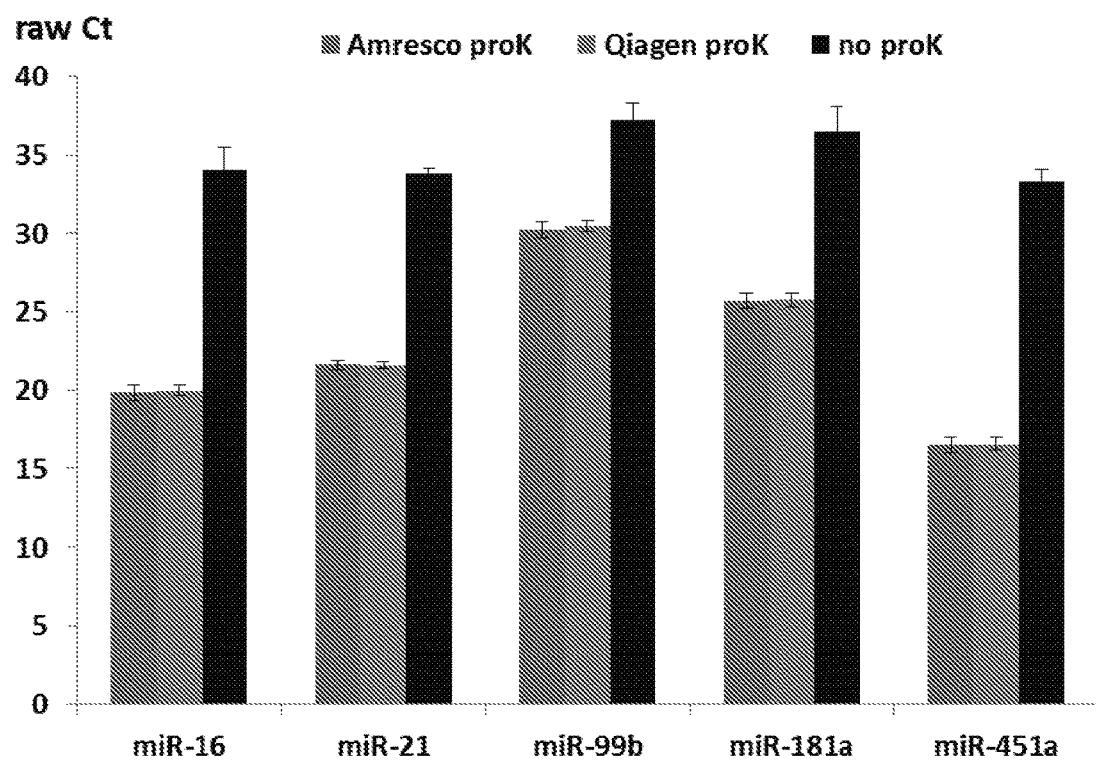
FIG. 8 presents data from testing whether using different sources of proteinase K impacted miRNA extraction.

Multiple steps of the improved protocol (see right side of FIG. 19) were then evaluated to see if additional changes would further increase the analytical sensitivity of the miRNA assay (performed on the miRNA extracted using the FOX miRNA extraction protocol) (FIG. 7). In other words, multiple steps were evaluated individually to improve the protocol even further:

1. Eluted in less elution buffer to concentrate the RNA and to mimic automation process
2. Added two FOX wafers (dissolvable films having ferric oxide particles) instead of a single film; conclusion=no change
3. Added Proteinase K prior to adding the diluent; conclusion=decreased performance
4. Added Proteinase K in half the volume of diluent
5. Added less or more diluent; conclusion=didn't consistently increase sensitivity.
6. Added DNase; conclusion=the assay is DNase compatible.
7. Attempted additional 2× and 3× washes vs. one wash; conclusion=improves sensitivity The following protocol was used, with the exception of the tested conditions listed above:

Protocol Used
1. +850 µL HPV LBC Diluent and 70 µL Proteinase K to 200 µL serum;
2. 50° C. 10 min, 95° C. 10 min, then ice cool 2 min;
3. Transfer all sample to FOX extraction tube;
4. Wait 5 min, then pipette 10× for the film to dissolve;
5. +55 µL Binding Buffer, pipette 10× to mix;
6. Put on magnet, remove all liquid and bubbles;
7. +950 µL Wash Buffer, pipette 10× to mix;
8. Put on magnet, remove all liquid and bubbles;
9. +50 µL Elution Buffer, pipette 10× to mix;
10. Put on magnet, transfer 50 µL liquid to a new tube;
11. +5 µL 11× Neutralization Buffer to the new tube.

Additional experiments were then performed to determine whether changes in volume of the starting diluent, proteinase K, and/or Binding buffer further improved miRNA extraction. The data showed that using 700 µL of HPV LBC Diluent (compared to 850 µL), 60 µL of proteinase K (compared to 70 µL), and 47 µL of acidic binding buffer (compared to 55 µL) was equivalent or better.

Different sources of Proteinase K were then tested to evaluate whether the source of proteinase K impacted miRNA extraction (when using the improved miRNA extraction protocol—see above: used 700 µL of HPV LBC Diluent, 60 µL of proteinase K, and 47 µL of acidic binding buffer). The results are presented in FIG. 8. Proteinase K from either Amresco or Qiagen were equivalent, and both were much better than not using proteinase K.

Figure 9:
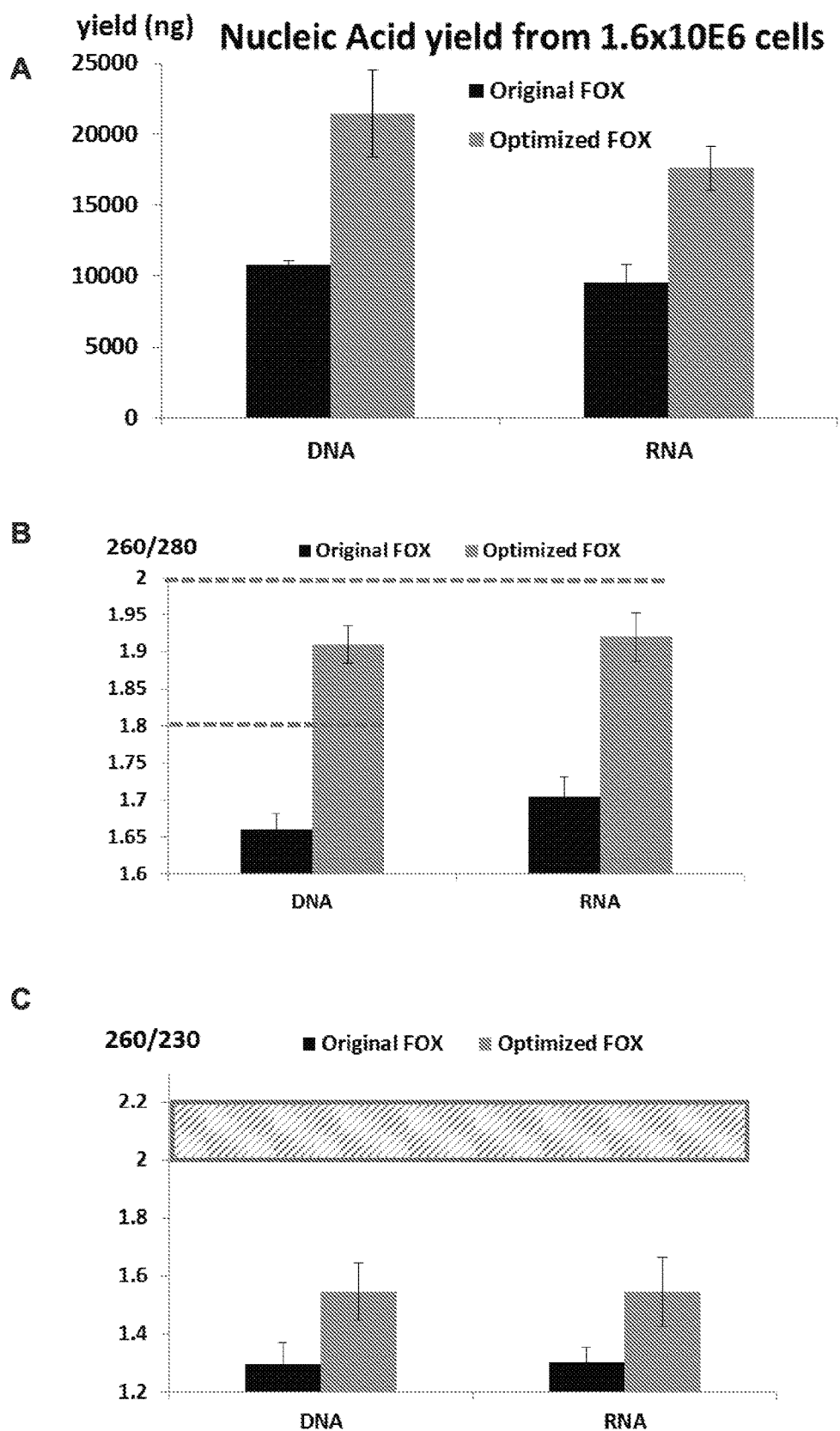
FIG. 9, Panels A-C. Human colon cancer (HCT15) cells were cultured and 1.6×10E6 cells were harvested. Left column represents results for DNA and RNA extraction using the original ferric oxide (FOX) protocol (left column), or the improved protocol above (right column). (Panel A) Yield of both DNA and RNA significantly increased when using the improved protocol. (Panel B) The depicted graph demonstrates the high purity of both DNA and RNA that was extracted from human colon cancer (HCT15) cells using the improved method. (Pure nucleic acid is typical when A260/280 ratio is greater than 1.8) (Panel C) The depicted graph demonstrates that reduced impurities (likely salts) remain in purified DNA or RNA extracted from human colon cancer (HCT15) cells using the improved protocol.
Figure 10:
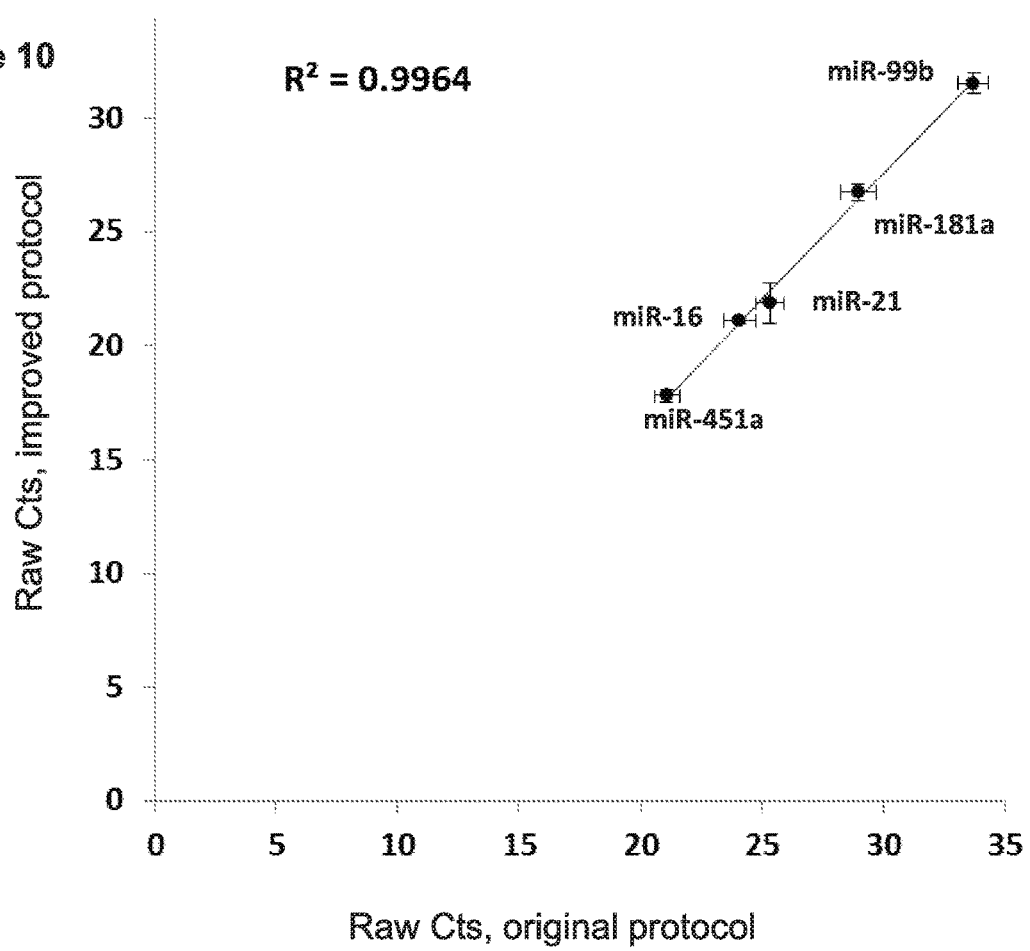
FIG. 10 presents a comparison of raw Cts obtained when measuring (using qPCR) 5 different example miRNAs from nucleic acids extracted using the old protocol (see left side of FIG. 19) versus the improved protocol.

Example 3—Comparisons (FIGS. 9-10)

The data presented in FIG. 9 demonstrate that the improved FOX extraction protocol improves the quantity and quality of DNA and RNA.

FIG. 9. (Panels A-C) Human colon cancer (HCT15) cells were cultured and 1.6×10E6 cells were harvested. Left column represents results for DNA and RNA extraction using the original ferric oxide (FOX) protocol (left column), or the improved protocol above (right column). (Panel A) Yield of both DNA and RNA significantly increased when using the improved protocol. (Panel B) The depicted graph demonstrates the high purity of both DNA and RNA that was extracted from human colon cancer (HCT15) cells using the improved method. [Pure nucleic acid is typical when A260/280 ratio is greater than 1.8] (Panel C) The depicted graph demonstrates that reduced impurities (likely salts) remain in purified DNA or RNA extracted from human colon cancer (HCT15) cells using the improved protocol.

The data presented in FIG. 10 show a comparison of raw Cts obtained when measuring (using qPCR) 5 different example miRNAs from nucleic acids extracted using the old protocol (see left side of FIG. 19) versus the improved protocol. The Cts were 2.8 lower on average for the improved protocol versus the original protocol (lower Cts indicates that the measured RNAs were more abundant in the sample and/or the sample allowed for better sensitivity).

Example 4—can Efficiently Extract Nucleic Acid (e.g., mRNA and miRNA) from Multiple Different Sample Types (FIGS. 11-16)

Nucleic acids were successfully extracted from: (i) serum and plasma; (ii) freshly cultured cells (e.g., Human Prostate Cancer (PC3) cells, Androgen-Sensitive Human Prostate Adenocarcinoma (LNCaP) Cells, and Human Colon Tumor (HCT15) cells); (iii) BD SurePath-preserved cells (e.g., HCT15 cells)(e.g., preserved for 7 days); (iv) formalin-fixed paraffin embedded tissue (FFPE)(e.g., archived (5-year) human colon adenocarcinoma samples, and archived human non-small cell lung cancer samples); and (v) whole blood (e.g., collected in BD PAXgene tubes). The amounts of 5 different miRNAs (miR-16, miR-21, miR-99b, miR-181a, and miR-451a) were measured from the samples using qPCR, and the particular miRNAs were chosen because they represent a range of both abundant and rare miRNA in tissue. For the whole blood sample, mRNA was measured from the extracted nucleic acids.

Figure 11:
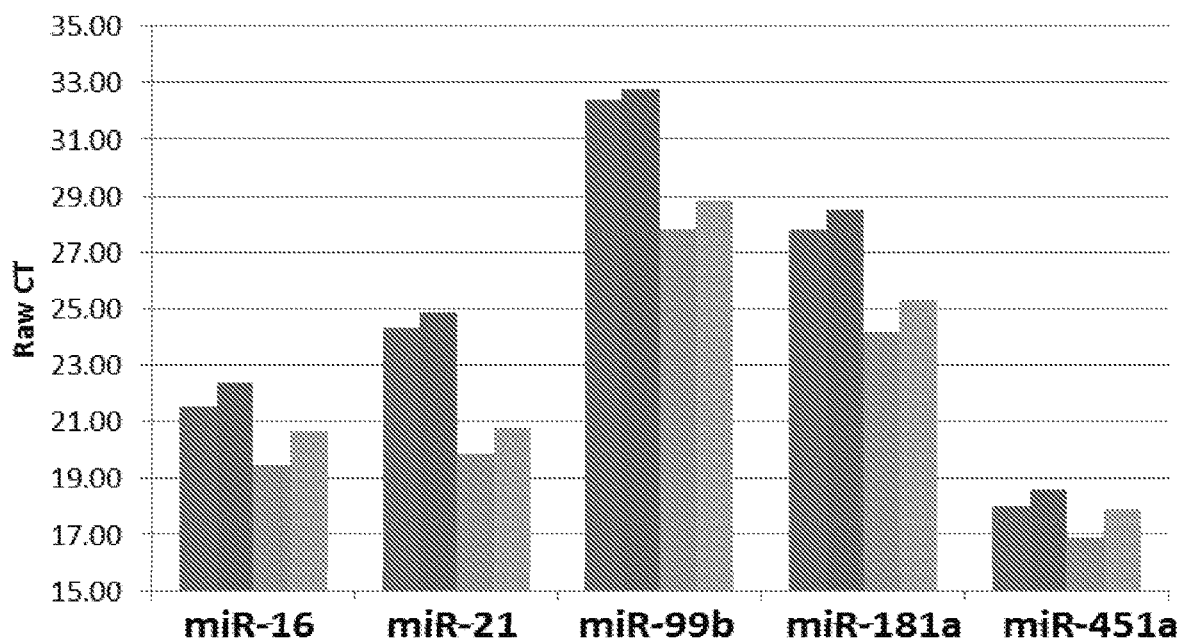
FIG. 11 presents data from experiments in which serum and plasma nucleic acids were extracted using either the original FOX or improved FOX extraction protocols. The amounts of 5 different miRNAs (miR-16, miR-21, miR-99b, miR-181a, and miR-451a) were measured from the samples using qPCR. For each miRNA: the first bar on the left represents a serum sample in which RNA was extracted using the improved protocol; the second bar represents a serum sample in which RNA was extracted using the original protocol; the third bar represents a plasma sample in which RNA was extracted using the improved protocol; and the fourth bar represents a plasma sample in which RNA was extracted using the original protocol

FIG. 11. Serum and plasma nucleic acids were extracted using either the original FOX or improved FOX extraction protocols. The amounts of 5 different miRNAs (miR-16, miR-21, miR-99b, miR-181a, and miR-451a) were measured from the samples using qPCR. As demonstrated, the improved protocol yields 4× to 16× fold more miRNA when compared to the original protocol (left side FIG. 19). For each miRNA: the first bar on the left represents a serum sample in which RNA was extracted using the improved protocol; the second bar represents a serum sample in which RNA was extracted using the original protocol; the third bar represents a plasma sample in which RNA was extracted using the improved protocol; and the fourth bar represents a plasma sample in which RNA was extracted using the original protocol.

Figure 12:
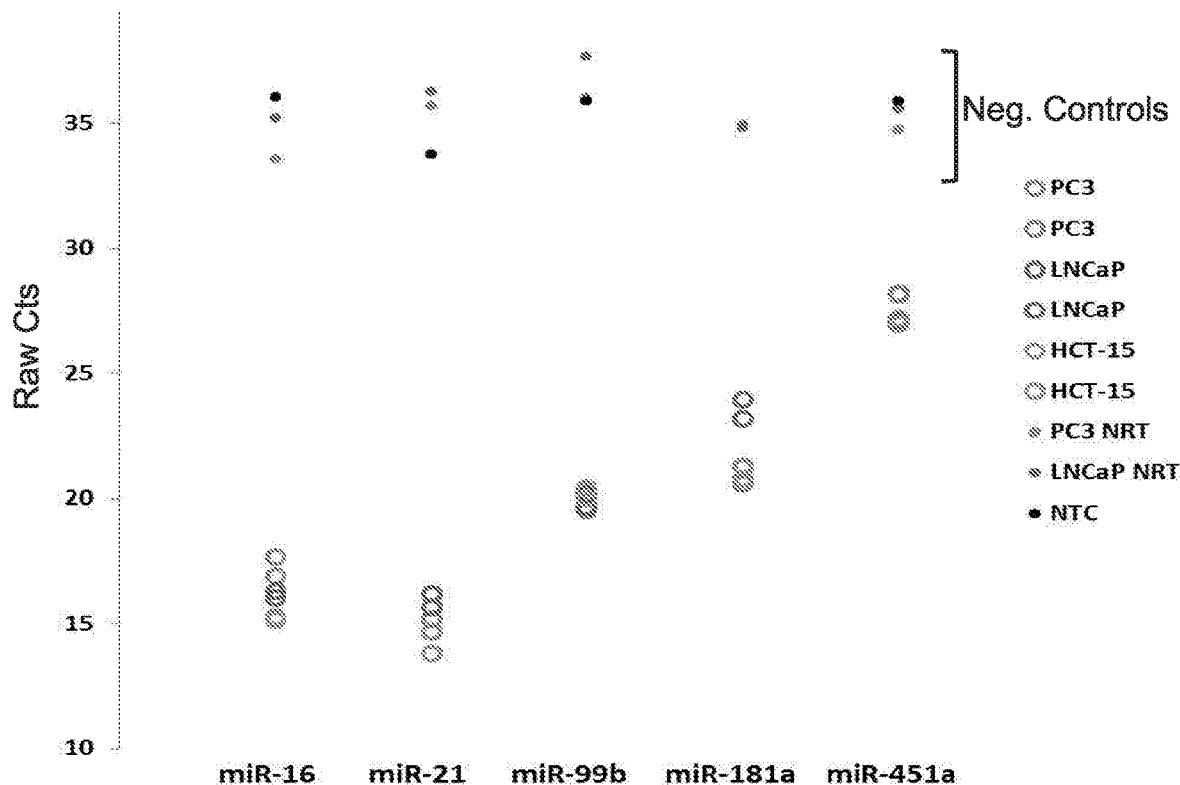
FIG. 12 presents data from experiments in which various human cancer cell lines (PC3, LNCaP, and HCT15) were cultured, pelleted, and re-suspended in 200 uL water, and then the improved FOX protocol used to extract nucleic acids. The amounts of 5 different miRNAs (miR-16, miR-21, miR-99b, miR-181a, and miR-451a) were measured from the samples using qPCR. Specificity was determined using no template (NTC) and minus reverse transcriptase controls (NRT).

FIG. 12. Various human cancer cell lines (PC3, LNCaP, and HCT15) were cultured, pelleted, and re-suspended in 200 uL water, and then the improved FOX protocol used to extract nucleic acids. The amounts of 5 different miRNAs (miR-16, miR-21, miR-99b, miR-181a, and miR-451a) were measured from the samples using qPCR. Specificity was determined using no template (NTC) and minus reverse transcriptase controls (NRT).

Figure 13:
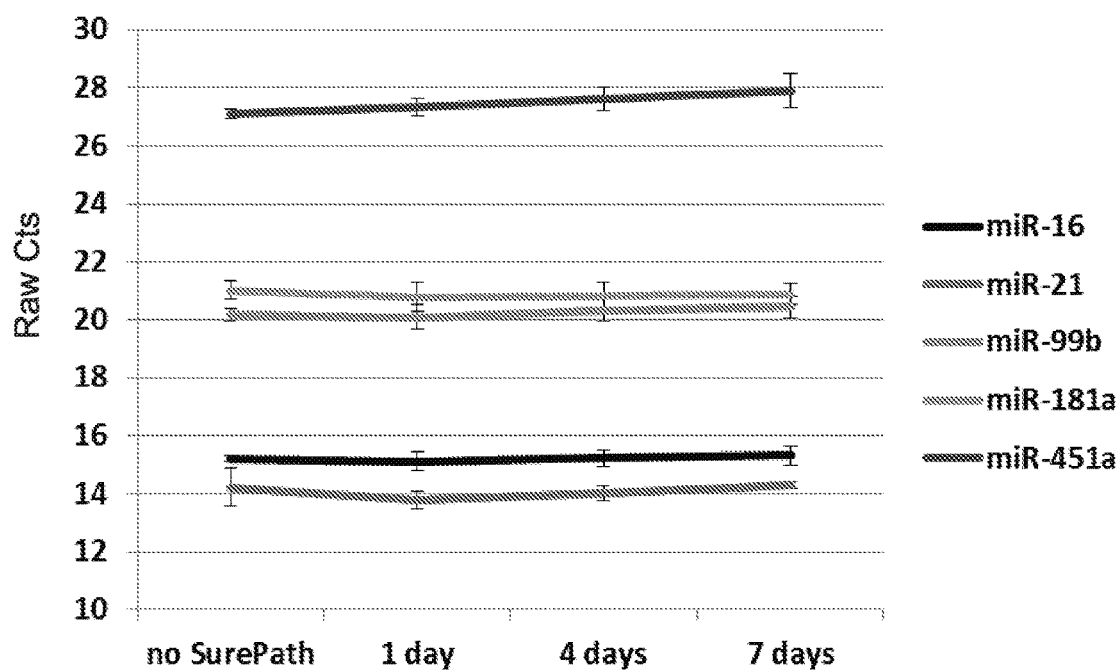
FIG. 13 presents data from experiments in which nucleic acids were extracted (using the improved FOX protocol) from BD SurePath-preserved cells (HCT15 cells) that were preserved for different amounts of time. The amounts of 5 different miRNAs (miR-16, miR-21, miR-99b, miR-181a, and miR-451a) were measured from the samples using qPCR.

FIG. 13. Nucleic acids were extracted (using the improved FOX protocol) from BD SurePath-preserved cells (HCT15 cells) that were preserved for different amounts of time. The amounts of 5 different miRNAs (miR-16, miR-21, miR-99b, miR-181a, and miR-451a) were measured from the samples using qPCR.

Figure 14:
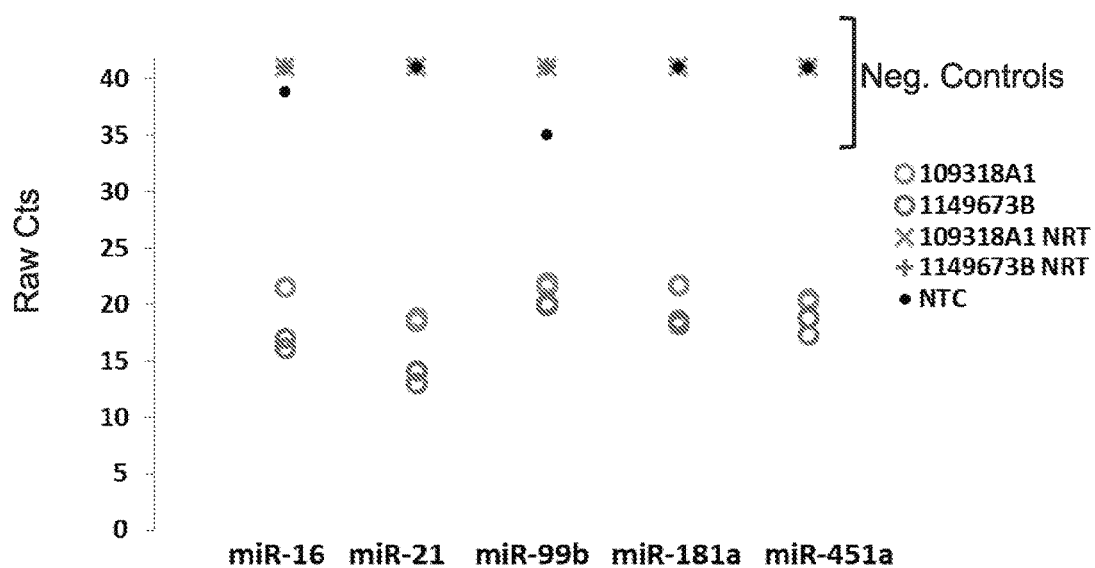
FIG. 14 presents data from experiments in which nucleic acids were extracted (using the improved FOX protocol) from formalin-fixed paraffin embedded tissue (FFPE): archived (5-year) human colon adenocarcinoma samples (Top), and archived human non-small cell lung cancer (NSCLC) samples (Bottom). For each patient sample, three 10 um tissue sections were pooled prior to RNA extraction. Age of the tissue blocks ranged from 3 to 5 years old. The amounts of 5 different miRNAs (miR-16, miR-21, miR-99b, miR-181a, and miR-451a) were measured from the samples using qPCR.
Figure 14:
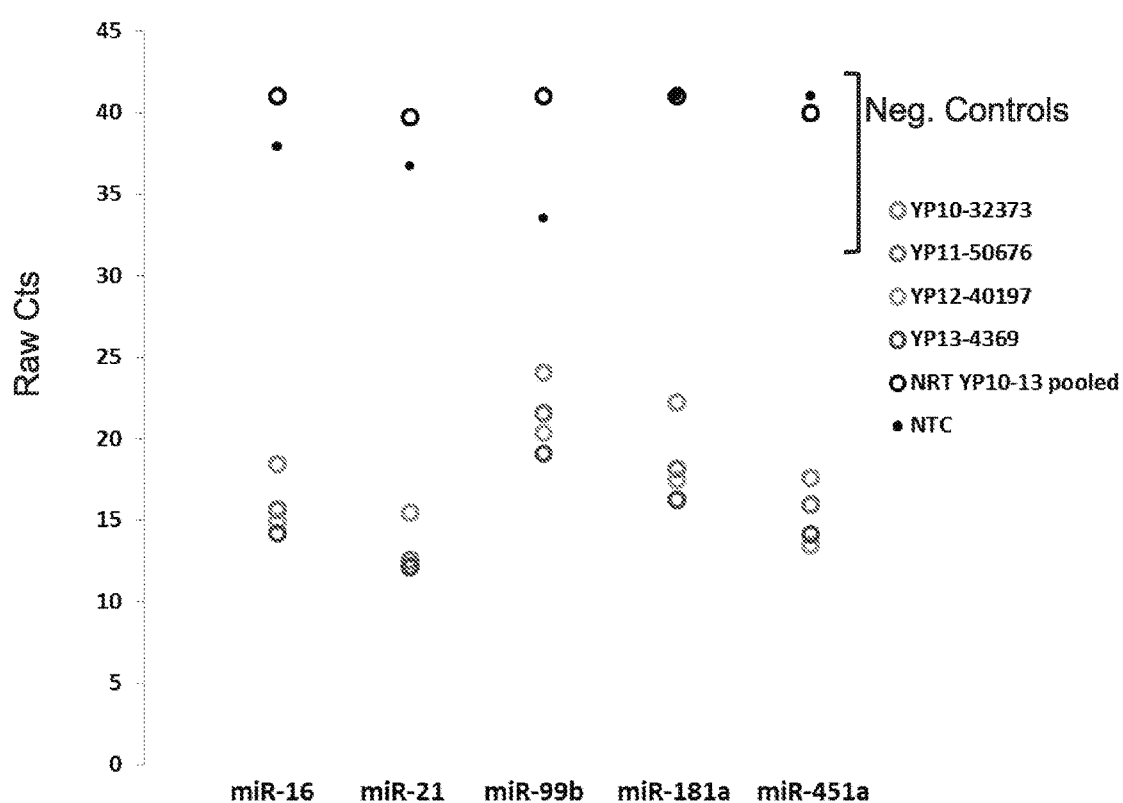

FIG. 14. Nucleic acids were extracted (using the improved FOX protocol) from formalin-fixed paraffin embedded tissue (FFPE): archived (5-year) human colon adenocarcinoma samples (Top), and archived human non-small cell lung cancer (NSCLC) samples (Bottom). For each patient sample, three 10 um tissue sections were pooled prior to RNA extraction. Age of the tissue blocks ranged from 3 to 5 years old. The amounts of 5 different miRNAs (miR-16, miR-21, miR-99b, miR-181a, and miR-451a) were measured from the samples using qPCR. As demonstrated, specific miRNAs were detected by qPCR from nucleic acid (miRNA) extracted from the FFPE tissue blocks. NTC=no template control and YP10-13 pooled NRT=template RNA but no reverse transcriptase added to act as another negative control.

Figure 15:
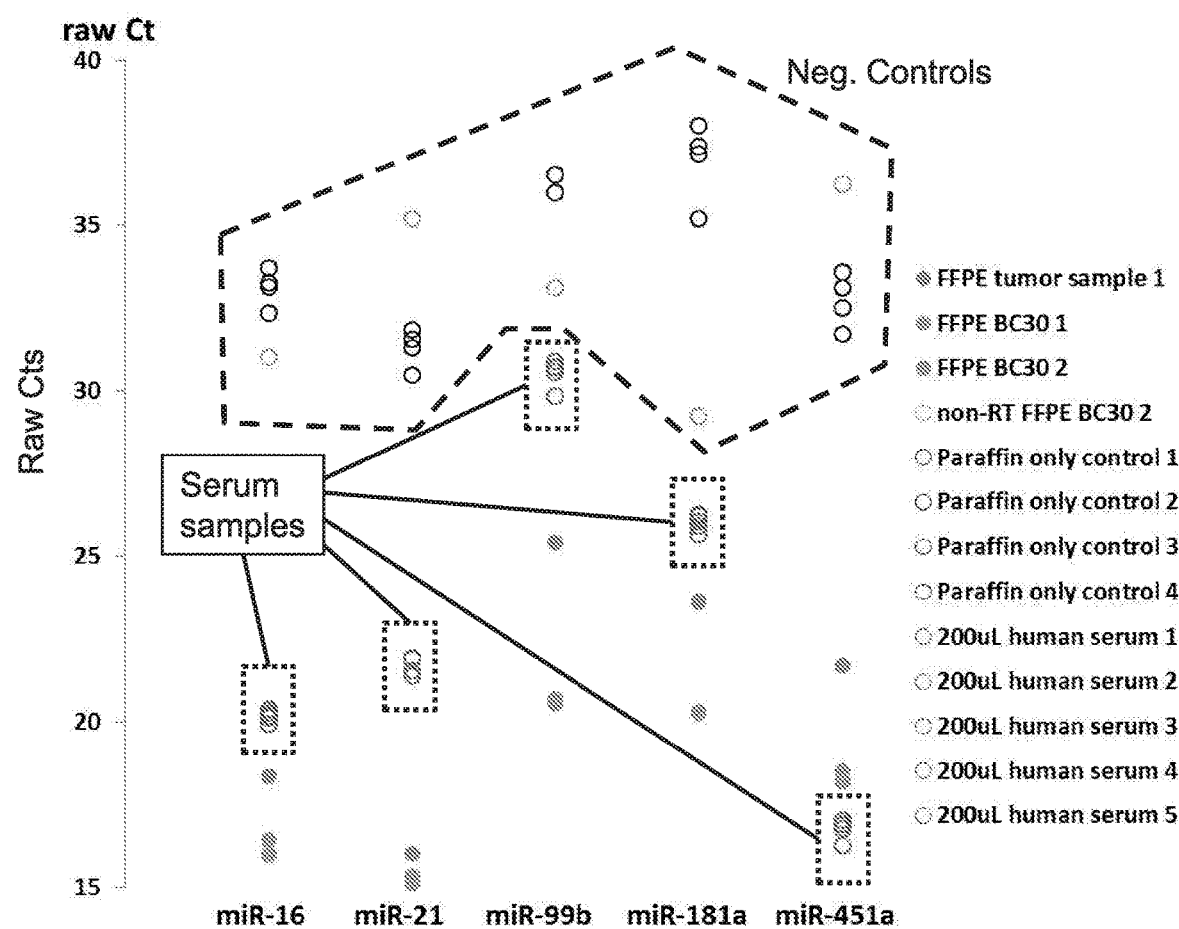
FIG. 15 presents data from experiments in which nucleic acids were extracted (using the improved FOX protocol) from formalin-fixed paraffin embedded tissue (FFPE) and from human serum samples. The amounts of 5 different miRNAs (miR-16, miR-21, miR-99b, miR-181a, and miR-451a) were measured from the samples using qPCR.

FIG. 15. Nucleic acids were extracted (using the improved FOX protocol) from formalin-fixed paraffin embedded tissue (FFPE) and from human serum samples. The amounts of 5 different miRNAs (miR-16, miR-21, miR-99b, miR-181a, and miR-451a) were measured from the samples using qPCR. As demonstrated, specific miRNAs were detected by qPCR from nucleic acid (miRNA) extracted from the FFPE tissue blocks and from human serum samples.

Figure 16:
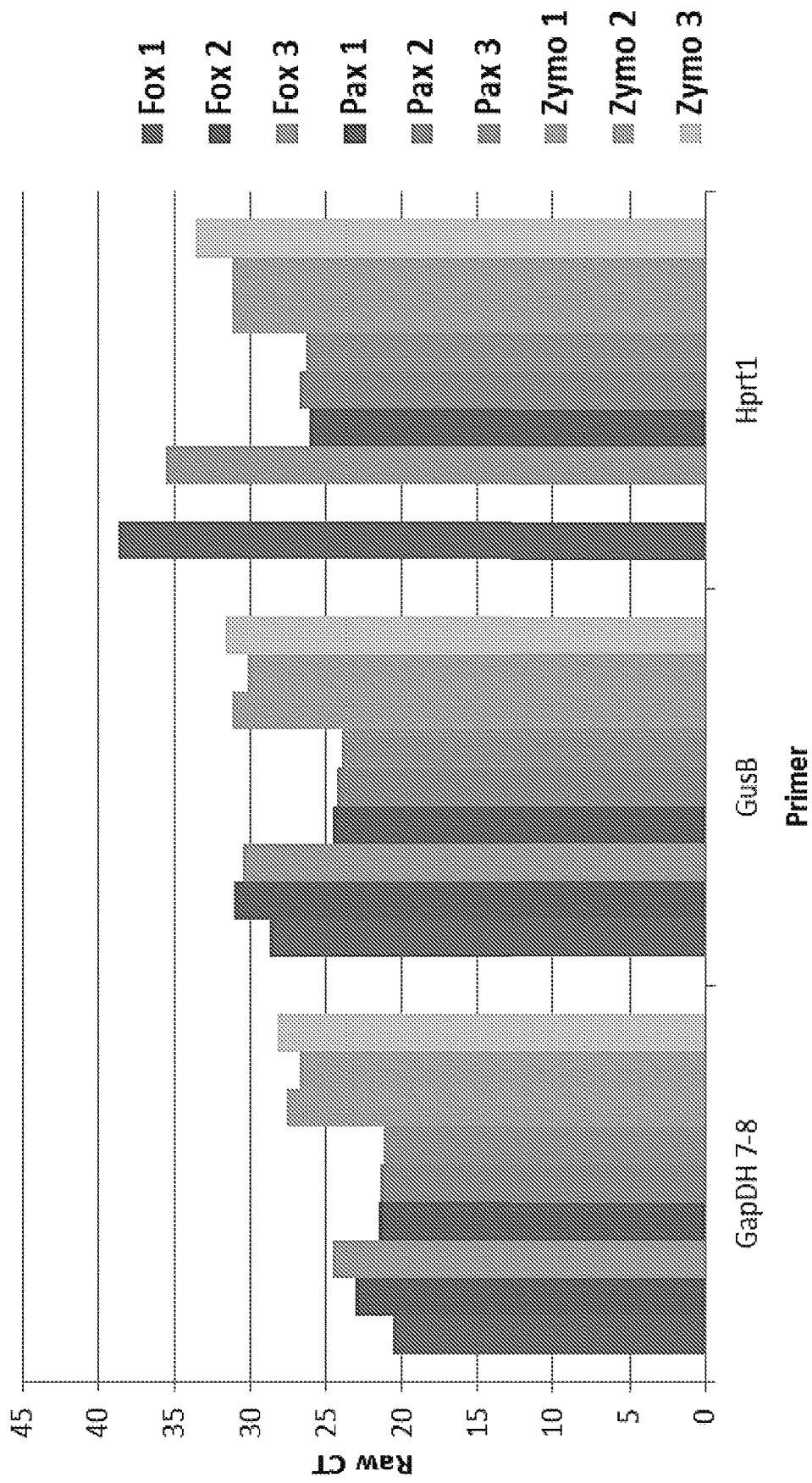
FIG. 16 presents data from experiments in which patient blood was pooled and 200 uL of processed sample was used to extract mRNA using three different methods from peripheral blood: (i) improved FOX protocol to extract nucleic acids (left three bars for each mRNA); Paxgene per protocol (middle three bars for each mRNA), and Zymo Whole Blood RNA (right three bars for each mRNA). Standard qPCR was performed to measure mRNA using SuperScript III and primers specific to GAPdH (spanning exons 7-8), GusB, and Hprt1.

FIG. 16. Whole blood was drawn from the patient then stabilized in PreAnalytiX PAXgene Blood RNA Tubes. Patient blood was pooled and 200 uL of processed sample was used to extract mRNA using three different methods from peripheral blood: (i) improved FOX protocol to extract nucleic acids (left three bars for each mRNA); Paxgene per protocol (middle three bars for each mRNA), and Zymo Whole Blood RNA (right three bars for each mRNA). Standard qPCR was performed to measure mRNA using SuperScript III and primers specific to GAPdH (spanning exons 7-8), GusB, and Hprt1. The data demonstrate that nucleic acids (e.g., mRNA) can be extracted and measured from whole blood (e.g., PAXgene stabilized whole blood) using the improved FOX protocol.

Figure 17:
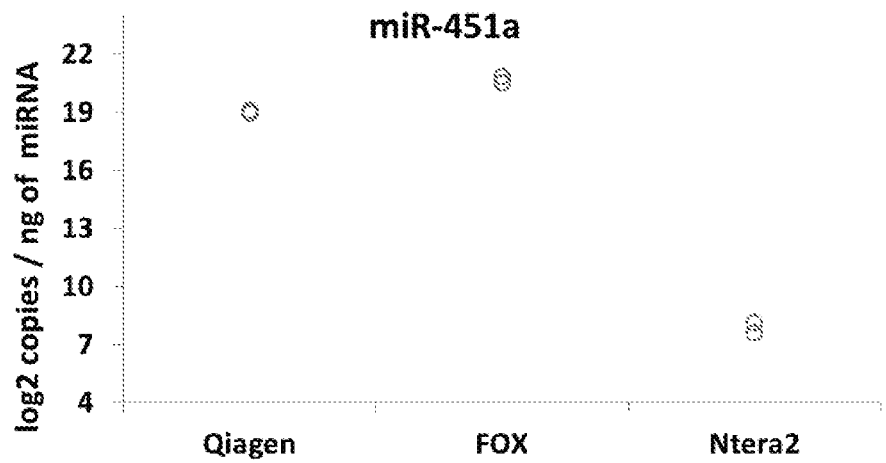
FIG. 17 presents data from experiments in which microRNA was extracted using the improved FOX protocol from 200 uL of frozen serum. 4 ng or ~$10^3$ copies per ng used in qPCR.
Figure 17:
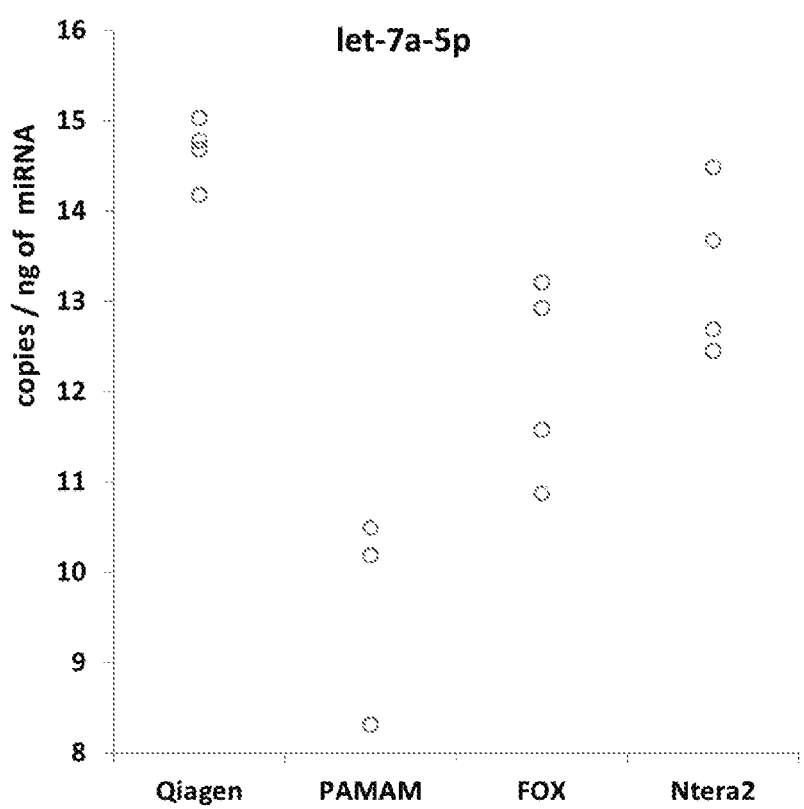
Figure 18:
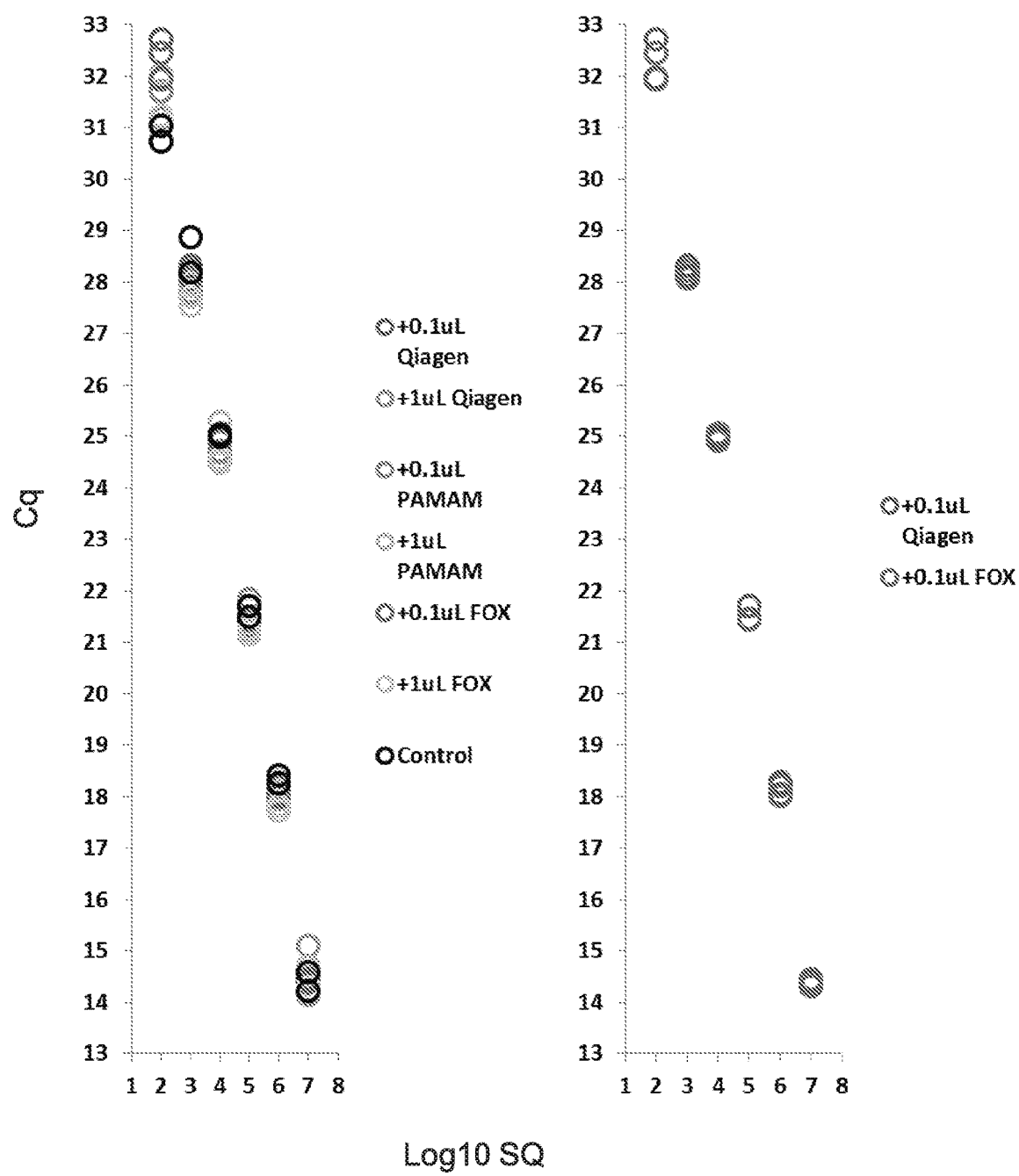
FIG. 18, Panels A-B present data from experiments in which varying amounts of total RNA was added to each miR-99b qPCR reaction to determine if carry over salts from either the improved FOX protocol or the other tested extraction methods were inhibitory. The data are presented in two ways (Panel A and Panel B).
Figure 18:
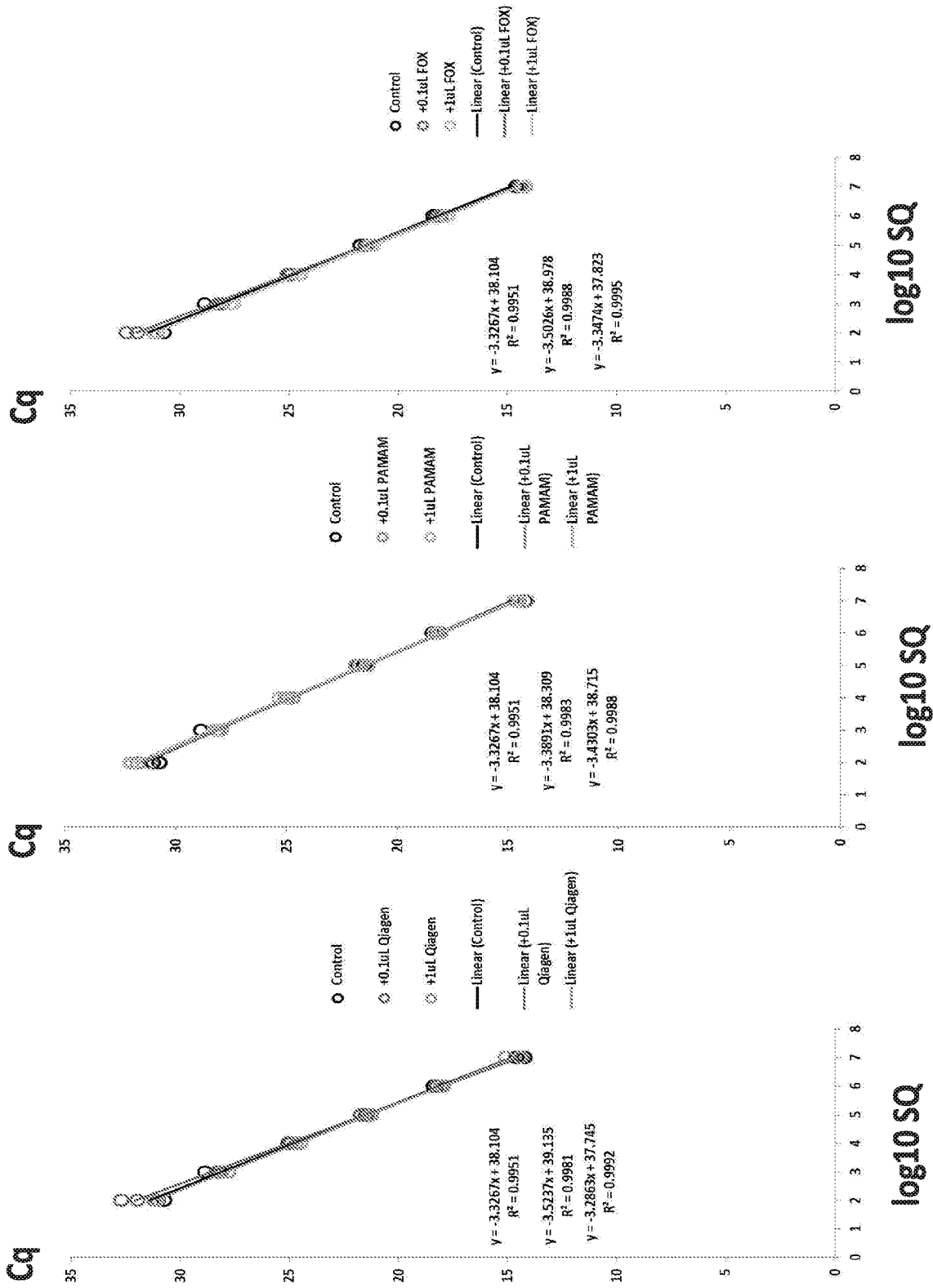

Example 5—Example Applications (FIGS. 17-18)

MicroRNAs were chosen that could be used to develop an in vitro diagnostic test for breast cancer. Experiments were performed to test whether the selected miRNAs were detectable after extraction (from patient breast cancer serum samples) with the improved FOX extraction protocols described herein, compared to other protocols (Qiagen, PAMAM, Ntera), which are less efficient. The data are present in FIG. 17 as the abundance (copies/ng of total miRNA) of each target miRNA as detected by qPCR (MiRXES).

The data demonstrated that the selected miRNAs could be measured from nucleic acids extracted from breast cancer patient serum using the improved FOX protocols described herein. All 17 of the selected miRs were detected from the nucleic acids extracted using the improved FOX protocols described herein. The improved FOX protocol performed at least as good as, and even better than, the other tested extraction methods.

FIG. 17. MicroRNA was extracted using the improved FOX protocol from 200 uL of frozen serum. 4 ng or ~$10^3$ copies per ng used in qPCR.

FIG. 18. Varying amounts of total RNA was added to each miR-99b qPCR reaction to determine if carry over salts from either the improved FOX protocol or the other tested extraction methods were inhibitory. Linearity or R-squared values were comparable between the extraction methods. There was no significant inhibition from residual chemicals/components present in the extracted samples. The data are presented in two ways (panel A and panel B).

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method of generating a sample of extracted microRNAs from an initial biological sample, the method comprising:
   (a) contacting the initial biological sample comprising microRNAs with proteinase K at a temperature in a range of from 47° C. to 53° C. for a period of time in a range of from 10 to 40 minutes, to degrade proteins present in the sample, thereby producing a proteinase K treated sample;
   (b) contacting the proteinase K treated sample with ferric oxide particles under acidic conditions to induce binding between the ferric oxide particles and the microRNAs;
   (c) magnetically separating the microRNA bound ferric oxide particles from the proteinase K treated sample;
   (d) contacting the microRNA bound ferric oxide particles with an alkaline elution buffer to release the microRNAs from the ferric oxide particles into the alkaline elution buffer, thereby generating an alkaline microRNAs sample; and
   (e) magnetically separating the ferric oxide particles from the alkaline microRNA sample,
   to generate a sample of extracted microRNAs.

2. The method of claim 1, further comprising, after the magnetically separating of step (e), neutralizing the alkaline microRNA sample by contacting the alkaline microRNA sample with a buffered solution to generate the sample of extracted microRNA.

3. The method of claim 1, wherein the proteinase K treated sample is contacted in step (b) with a dissolvable film comprising the ferric oxide particles, whereby the film dissolves and releases the ferric oxide particles.

4. The method of claim 3, wherein the film is formed from a material comprising one or more of: hydroxyalkylmethyl cellulose; carboxymethyl cellulose; carboxylic hydroxyalkyl ester monomer; ethoxylated hydroxyalkyl(meth)acrylate; propoxylated hydroxyalkyl(meth)acrylate; polyethylene glycol (PEG); polyvinyl alcohol (PVA); and combinations thereof.

5. The method of claim 1, further comprising a step of identifying a biomolecule that is bound to one or more of the microRNAs.

6. The method of claim 1, wherein the method does not include use of chloroform or phenol.

7. The method of claim 1, wherein the method is completed in a range from 10 minutes to 30 minutes.

8. The method of claim 1, wherein the method further comprises depleting an abundant microRNA from the proteinase K treated sample prior to step (b) and/or after step (e).

9. The method of claim 8, wherein the abundant microRNA is selected from the group consisting of: miR-191, miR-320, miR-29b, miR-143, miR-145, and miR-424.

10. The method of claim 8, wherein the depleting comprises (i) contacting the proteinase K treated sample with ferric oxide particles that are conjugated to a nucleic acid probe that hybridizes with the abundant microRNA, and (ii) separating the probe-conjugated ferric oxide particles, hybridized with the abundant microRNA, from the proteinase K treated sample.

* * * * *